(12) United States Patent
Roques et al.

(10) Patent No.: US 7,582,797 B2
(45) Date of Patent: Sep. 1, 2009

(54) DERIVATIVES OF 4,4'-DITHIOBIS-(3-AMINOBUTANE-1-SULFONATES) AND COMPOSITIONS COMPRISING THE SAME

(75) Inventors: Bernard Pierre Roques, Paris (FR); Nicolas Inguimbert, Cachan (FR); Marie-Claude Fournie-Zaluski, Paris (FR); Pierre Corvol, Paris (FR); Catherine Llorens-Cortes, Burnes sur Yvette (FR)

(73) Assignee: Institute National de la Sante et de la Recherche Medicale (Inserm), Paris Cedex (FR)

( * ) Notice: Subject to any disclaimer, the term of this patent is extended or adjusted under 35 U.S.C. 154(b) by 115 days.

(21) Appl. No.: 10/567,362

(22) PCT Filed: Aug. 6, 2004

(86) PCT No.: PCT/FR2004/002106

§ 371 (c)(1),
(2), (4) Date: Feb. 6, 2006

(87) PCT Pub. No.: WO2005/014535

PCT Pub. Date: Feb. 17, 2005

(65) Prior Publication Data

US 2006/0205695 A1    Sep. 14, 2006

(30) Foreign Application Priority Data

Aug. 6, 2003    (FR) .................................. 03 09700

(51) Int. Cl.
*C07C 321/14*    (2006.01)

(52) U.S. Cl. ...................................... 564/500

(58) Field of Classification Search ................... 564/500
See application file for complete search history.

(56) References Cited

OTHER PUBLICATIONS

Cancer and Metastasis Reviews (1998), 17(1), 91-106.*
Science (1999), vol. 286, 531-537.*
Cancer [online], [retrieved on Jul. 6, 2007] Retrieved from the Internet, URL; http://www nlm. nih. gov/medlineplus/cancer.html>.*
Cancer [online], [retrieved on Jul. 6, 2007]. Retrieved from the Internet, URL; http://en.wikipedia.org/wiki/Cancer>.*
Cecil Textbook of Medicine, 20th edition (1996), vol. 2, pp. 2050-2057.*
Cecil Textbook of Medicine, 20th edition (1996), vol. 2, pp. 1992-1996.*
FDA mulls drug to slow late-stage Alzheimer's [online], [retrieved on Sep. 23, 2003]. Retrieved from the Internet, URL; http://www.cnn.com/2003/HEAL TH/condtions/09/24/alzheimers.drug.ap/indexhtml>.*
RN 85550-11-4; retrieved from CAPLUS on Apr. 14, 2009.*
Chauvel, Eric, N. et al., "Differential Inhibition of Aminopeptidase A and Aminopeptidase N by New β-Amino Thiols" J. Med. Chem, (1994), vol. 37, pp. 2950-2957.
Chauvel, Eric, N. et al., "Investigation of the Active Site of Aminopeptidase A Using a Series of New Thiol-Containing Inhibitors", J. Med. Chem, (1994), vol. 37, pp. 1339-1346.
Martin, L., et al., β-Amino-thiols Inhibit the Zinc Metallopeptidase Activity of Tetanus Toxin Light Chain, J. Med. Chem, (1998), vol. 41, pp. 3450-3460.

* cited by examiner

*Primary Examiner*—Rebecca L Anderson
*Assistant Examiner*—Shawquia Young
(74) *Attorney, Agent, or Firm*—Browdy and Neimark, P.L.L.C.

(57) ABSTRACT

The invention relates to derivatives of 4,4'-dithiobis-(3-aminobutane-1-sulfonates) of formula (1), of use for the treatment and prevention of primary and secondary arterial hypertension.

16 Claims, No Drawings

DERIVATIVES OF 4,4'-DITHIOBIS-(3-AMINOBUTANE-1-SULFONATES) AND COMPOSITIONS COMPRISING THE SAME

The present invention relates to novel compounds, to processes for preparing these compounds, to pharmaceutical formulations comprising these compounds, and to the therapeutic use of these compounds. The present invention relates in particular to compounds that are of use in the treatment and prevention of primary and secondary arterial hypertension, of an ictus, of myocardial ischemia, of cardiac insufficiency and renal insufficiency, of myocardial infarction, of a peripheral vascular disease, of diabetic protinuria, of syndrome X and of glaucoma.

Arterial hypertension is a condition for which the causes remain generally unknown. Extrinsic factors which may contribute include obesity, a sedentary lifestyle, excessive alcohol or salt intake and stress. Intrinsic factors suggested as factors that play a role include fluid retention, sympathetic nervous system activity and blood vessel constriction. Arterial hypertension can contribute directly or indirectly to heart disease, peripheral and cerebral vascular system diseases, and brain, eye and kidney diseases.

The treatment of arterial hypertension comprises the use of diuretic agents, of adrenergic blocking agents, of angiotensin-converting enzyme inhibitors, of angiotensin receptor antagonists, of calcium antagonists and of direct vasodilators. However, a certain number of patients remain refractory to all the treatments, thus worsening the risk of various diseases related to their hypertension, and in particular the setting in of chronic heart failure. It is therefore desirable to identify novel compounds for the treatment of arterial hypertension.

The present inventors have identified novel compounds which are effective in reducing arterial hypertension and which, thus, are of use in the treatment of arterial hypertension and of diseases to which they directly and indirectly contribute.

These compounds behave in particular like powerful inhibitors of aminopeptidase A (also called APA or EC 3.4.11.7), which is a zinc metallopeptidase that is very conserved from one species to another, including humans. It has been demonstrated that APA acts on the central regulation of arterial pressure (A. Reaux et al., *Proc. Natl. Acad. Sci. USA*, 1999, 96, 13415-13420 and M. C. Fournié-Zaluski et al., *Proc. Natl. Acad. Sci. USA* 2004; 101; 7775-7780). The present invention shows that, unexpectedly, the introduction of a group $R_2$ onto a nonpeptide structure results in the production of APA-inhibiting compounds that have a high affinity and selectivity for APA, whereas these compounds have no activity with respect to another aminopeptidase, aminopeptidase N (APN).

Consequently, the present invention comprises compounds of formula (1):

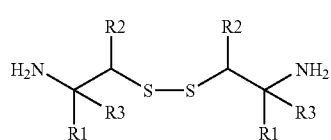

(1)

in which each group $R^1$ is identical to the other group $R^1$ and represents:

a $C_1$ to $C_6$ alkyl, $C_2$ to $C_6$ alkenyl or $C_2$ to $C_6$ alkynyl group, a $(CH_2)_n$benzyl group in which n is equal to 0 or 1, a $(CH_2)_m(C_3$ to $C_6$ cycloalkyl) group in which m is equal to 0 or 1, each of the alkyl, alkenyl, alkynyl, benzyl or cycloalkyl groups being substituted with one or two group(s) represented by the group A.

The group A represents:

a carboxylate group COOH or COOR, R representing a $C_1$ to $C_6$ alkyl or $CH_2$phenyl group;

a sulfonate group $SO_3H$ or $SO_3R'$, R' representing a $C_1$ to $C_6$ alkyl or $CH_2$phenyl group;

a phosphonate group $PO_3H_2$ or $PO_3R_2''R'''$, R'' and R''' independently representing H, or a $C_1$ to $C_6$ alkyl or $CH_2$phenyl group;

each group $R^2$ is identical to the other group $R^2$ and represents a $C_1$ to $C_6$ alkyl, $C_2$ to $C_6$ alkenyl or $C_2$ to $C_6$ alkynyl group, each alkyl, alkenyl or alkynyl group being free or substituted with the group B.

The group B represents:

a carboxylate group, COOH or COOR', R' representing a $C_1$ to $C_6$ alkyl or $CH_2$phenyl group;

a phenyl group that is free or substituted with one or more radicals chosen from a halogen atom, an optionally protected hydroxyl radical, a $C_1$ to $C_4$ alkyl group, a cyano group, a free, salified or esterified carboxyl group or an amide group.

Each group $R^3$ is identical to the other group $R^3$ and represents a hydrogen atom.

Preferred compounds (1) according to the invention are those in which $R^1$ is chosen from $C_1$ to $C_6$ alkyl, $C_2$ to $C_6$ alkenyl and benzyl groups, each of these groups being substituted with one or two group(s) represented by the group A and/or in which $R^2$ is chosen from a $C_1$ to $C_6$ alkyl group and a $C_2$ to $C_6$ alkenyl group, it being possible for each of these groups to be substituted with one or two group(s) represented by the group B.

Other preferred compounds (1) according to the invention are those in which $R^1$ represents an ethyl group substituted with a sulfonic group, a phosphonic group or a carboxylic group, that is free, salified or esterified, and $R^2$ represents an ethyl group substituted with an optionally substituted phenyl group.

A particularly preferred compound (1) is 4,4'-dithiobis-(3, 3'-amino-6,6'-phenyl-1,1'-hexanesulfonic) acid, and in particular 4(S), 4'(S), 3(S), 3'(S)-4'-dithiobis-(3,3'-amino-6,6'-phenyl-1,1'-hexanesulfonic) acid.

In another aspect, a subject of the present invention is a method for the prevention or treatment of arterial hypertension and of directly and indirectly related diseases, comprising the administration of a therapeutically effective amount of a compound of the present invention. In another aspect, the present invention provides pharmaceutical compositions comprising a compound of the present invention, preferably in combination with a pharmaceutically acceptable diluent or support.

In another aspect, the present invention provides a compound of the present invention for use in therapeutics, and in particular in human medicine.

The invention also relates to the use of a compound of formula (1), as a selective inhibitor with regard to aminopeptidase A.

In another aspect, the present invention provides the use of a compound of the present invention, for producing a medicinal product for use in the treatment of arterial hypertension and of directly and indirectly related diseases.

In another aspect, the present invention provides a method of treating a patient suffering from arterial hypertension and from directly and indirectly related diseases, comprising the administration of a therapeutically effective amount of a compound of the present invention.

The present invention provides methods for the prevention or treatment of arterial hypertension and of diseases to which arterial hypertension directly or indirectly contributes. These diseases comprise heart disease, peripheral and cerebral vascular system diseases, and brain, eye and kidney diseases. In particular, the diseases comprise primary and secondary arterial hypertension, an ictus, myocardial ischemia, cardiac insufficiency and renal insufficiency, myocardial infarction, a peripheral vascular disease, diabetic protinuria, syndrome X, glaucoma, neurodegenerative diseases and memory disorders. Moreover, hypertension, in particular central hypertension, is possibly related to a vascular hyperexpression of APA. The latter increases even more in tumors. As a result, the compounds of the present invention could have a therapeutic potential in the context of ischemic or tumoral pathologies (Marchio S, et al., Cancer Cell, 2004, 5:151-162).

The invention therefore also relates to the use of a compound of formula (1), for preparing a medicinal product for use in the treatment of ischemic or tumoral pathologies in which APA is involved.

As used in the present report, the expression "compound of the present invention" denotes a compound of formula (I) or one of its pharmaceutically acceptable salts or salvation products.

The expression "$C_1$ to $C_6$ alkyl", as used in the present report, denotes a hydrocarbon-based group with a straight or branched chain containing 1 to 6 carbon atoms. Examples of alkyl groups, in the manner used in the present report, include, but in a nonlimiting manner, methyl, ethyl, propyl, butyl, isopropyl, n-butyl and tert-butyl groups.

The expression "$C_2$ to $C_6$ alkenyl", as used in the present report, denotes a hydrocarbon-based group with a straight or branched chain having 1 to 6 carbon atoms, containing one or more double bonds. Examples of alkenyl groups, in the manner used in the present report, include, but in a nonlimiting manner, the vinyl group and similar groups.

The expression "$C_2$ to $C_6$ alkynyl", as used in the present report, denotes a hydrocarbon-based group with a straight or branched chain having 1 to 6 carbon atoms, containing one or more triple bonds. An example of an alkynyl group, in the manner used in the present report, includes, but in a nonlimiting manner, the ethynyl group.

The expression "$C_3$ to $C_6$ cycloalkyl" denotes a nonaromatic cyclic carbon-based ring having 3 to 6 carbon atoms. This ring may optionally contain up to 2 carbon-carbon double bonds. The cycloalkyl groups include, by way of example but not in a limiting manner, the cyclopentyl and cyclohexyl groups.

Preferably, $R^1$ is chosen from $C_1$ to $C_6$ alkyl, $C_2$ to $C_6$ alkenyl and benzyl groups substituted with one or two groups represented by the group A corresponding to the abovementioned definition.

Preferably, $R^2$ is chosen from $C_1$ to $C_6$ alkyl and $C_2$ to $C_6$ alkenyl groups, each alkyl or alkenyl group being optionally substituted with one or more groups represented by the group B defined above.

Although the preferred groups for each variable have in general been listed above separately for each variable, compounds of the present invention that are favored comprise those in which several variables or each variable in formula (I) are (is) chosen from the groups that are favored, more favored or preferred for each variable. Consequently, the present invention is intended to comprise all the combinations of favored, more favored and preferred groups.

Those skilled in the art will recognize that stereocenters exist in the compounds of formula (I). Consequently, the present invention comprises all the possible stereoisomers and geometric isomers of formula (I) and comprises not only racemic compounds but also the optically active isomers. When the compound of formula (I) is desired in the form of a single enantiomer, it can be obtained by resolution of the final product or by stereospecific synthesis from the isomerically pure starting material or else from any suitable intermediate. The resolution of the final product, of an intermediate or of a starting material can be carried out by any suitable process known in this field. See, for example, Stereochemistry of Carbon Compounds by E. I. Eliel (Mcgraw Hill, 1962) and Tables of Resolving Agents by S. H. Wilen. Furthermore, in cases where tautomeric forms of the compounds of formula (I) are possible, the present invention is intended to comprise all the tautomeric forms of the compounds.

A specialist in organic chemistry will note that many organic compounds can form complexes with solvents in which they are led to react or from which they are precipitated or crystallized. These complexes are known as "salvation products". For example, a complex with water is known as a "hydrate". The solvation products of the compound of formula (I) form within the scope of the present invention.

A specialist in organic chemistry will also note that many organic compounds can exist in more than one crystalline form. For example, the crystalline form may vary from one salvation product to another. Thus, all the crystalline forms of the compounds of formula (I) or of their pharmaceutically acceptable solvation products are included in the scope of the present invention.

Those skilled in the art will also note that the compounds of the present invention can equally be used in the form of one of their pharmaceutically acceptable salts or salvation products. The physiologically acceptable salts of the compounds of formula (I) comprise conventional salts formed from pharmaceutically acceptable inorganic or organic acids or bases and also quaternary ammonium addition salts. More specific examples of suitable acid salts comprise the salts formed with hydrochloric acid, hydrobromic acid, sulfuric acid, phosphoric acid, nitric acid, perchloric acid, fumaric acid, acetic acid, propionic acid, succinic acid, glycolic acid, formic acid, lactic acid, maleic acid, tartaric acid, citric acid, palmoic acid, malonic acid, hydroxymaleic acid, phenylacetic acid, glutamic acid, benzoic acid, salicylic acid, fumaric acid, toluenesulfonic acid, methanesulfonic acid, naphthalene-2-sulfonic acid, benzenesulfonic acid, hydroxynaphthoic acid, hydriodic acid, malic acid, steroic acid, tannic acid, etc. Other acids, such as oxalic acid, although they are not in themselves pharmaceutically acceptable, can be used in the preparation of salts that are of use as intermediates in obtaining the compounds of the present invention and their pharmaceutically acceptable salts. More specific examples of suitable basic salts comprise sodium salts, lithium salts, potassium salts, magnesium salts, aluminum salts, calcium salts, zinc salts, N,N'-dibenzylethylenediamine salts, chloropropane salts, choline salts, diethanolamine salts, ethylenediamine salts, N-methylglucamine salts and procaine salts. References hereinafter to a compound in accordance with the present invention concern both the compounds of formula (I) and their pharmaceutically acceptable salts and salvation products.

The compounds of the present invention and their pharmaceutically acceptable derivatives are suitably administered in the form of pharmaceutical compositions. These compositions can be suitably provided for the purposes of use in a conventional manner as a mixture with one or more physiologically acceptable carriers or excipients. The support(s) must be "acceptable" in the sense that they must be compatible with the other ingredients of the formulation and they must not be harmful to the individual receiving them.

Although it is possible to therapeutically administer the compounds of the present invention in the form of the crude chemical substance, it is preferable to provide the active ingredient in the form of a pharmaceutical formulation.

Consequently, the present invention also provides a pharmaceutical formulation comprising a compound of formula (I) or one of its pharmaceutically acceptable salts or solvation products in combination with one or more pharmaceutically acceptable carriers and, optionally, other therapeutic and/or prophylactic ingredients.

The formulations comprise those that are suitable for oral administration, parenteral administration (including subcutaneous administration, for example by injection or by means of a component to be deposited, intradermal administration, intrathecal administration, intramuscular administration, for example by deposition, and intravenous administration), rectal administration and topical administration (including dermal, buccal and sublingual administration), or in a form that is suitable for administration by inhalation or insufflation, although the most suitable route may depend, for example, on the recipient's state and affliction. The formulations may be suitably provided in a unit dosage form and may be prepared by any of the methods that are well known in the pharmacy field. All the methods comprise the step consisting in combining the compounds ("active ingredients") with the support which comprises one or more supplementary ingredients. In general, the formulations are prepared by combining the active ingredient uniformly and intimately with liquid carriers or finely divided solid supports or else with these two types of supports and subsequently, if necessary, fashioning the product into the desired formulation.

The formulations suitable for oral administration can be provided in the form of discreet units, such as capsules, cachets or tablets (for example, tablets to be chewed, in particular for pediatric administration), each containing a predetermined amount of the active ingredient; in the form of a powder or of granules; in the form of a solution or a suspension in an aqueous liquid or a nonaqueous liquid; or in the form of an oil-in-water liquid emulsion or a water-in-oil liquid emulsion. The active ingredient may also be provided in the form of a bolus, an electarium or a paste.

A tablet can be prepared by tableting or molding, optionally with one or more supplemental ingredients. Tablets produced by tableting can be prepared by tableting the active ingredient, in a suitable machine, in a free-flow form such as a powder or granules, optionally as a mixture with other conventional excipients, such as binders (for example, a syrup, gum arabic, gelatin, sorbitol, gum tragacanth, a starch mucilage, polyvinylpyrrolidone or hydroxymethylcellulose), fillers (for example, lactose, sucrose, microcrystalline cellulose, corn starch, calcium phosphate or sorbitol), lubricants (for example, magnesium stearate, stearic acid, talc, polyethylene glycol or silica), disintegrating agents (for example, potato flour or sodium starch glycolate) or wetting agents such as sodium lauryl sulfate. Molded tablets can be prepared by molding, in a suitable machine, a mixture of the compound reduced to powder, moistened with an inert liquid diluent. The tablets can be optionally coated or notched and can be formulated so as to bring about the slow or controlled release of the active ingredient which is therein. The tablets can be coated by means of processes that are well known in this field.

As a variant, the compounds of the present invention can be incorporated into liquid oral preparations such as aqueous or oily suspensions, solutions or emulsions, syrups or elixirs, for example. Furthermore, formulations containing these compounds can be provided in the form of dry products intended for reconstitution with water or another suitable carrier before use. These liquid preparations can contain conventional additives, such as suspending agents, for example sorbitol syrup, methylcellulose, glucose/sugar syrup, gelatin, hydroxyethylcellulose, carboxymethylcellulose, an aluminum stearate gel or hydrogenated edible fats; emulsifiers, such as lecithin, sorbitan monooleate or gum arabic; nonaqueous carriers (which may comprise edible oils), such as almond oil, fractionated coconut oil, oily esters, propylene glycol or ethyl alcohol; and preserving agents, such as methyl p-hydroxybenzoate, propyl p-hydroxybenzoate or sorbic acid. These preparations can also be formulated in the form of suppositories, containing, for example, conventional excipients for suppositories, such as cocoa butter or other glycerides.

The formulations for parenteral administration comprise aqueous and nonaqueous sterile injectable solutions which can contain antioxidants, buffers, bacteriostatic agents and solids which make the formulation isotonic with the blood of the selected recipient; and sterile aqueous and nonaqueous suspensions which can comprise suspending agents and thickeners. The formulations can be provided in single dose or multidose containers, for example hermetically closed ampoules and bottles, and can be stored in freeze-dried (lyophilized) form, requiring only the addition of a sterile liquid carrier, for example water for injectable preparations, immediately before use. Extemporaneous injectable solutions and suspensions can be prepared from sterile powders, granules and tablets of the type described above.

The formulations for rectal administration can be provided in the form of suppositories with the usual supports, such as cocoa butter, a hard fat or polyethylene glycol.

The formulations for topical administration in the buccal cavity, for example for buccal or sublingual administration, comprise lozenges comprising the active ingredient in a flavored excipient, such as sucrose and gum arabic or gum tragacanth, and pastilles comprising the active ingredient in an excipient such as gelatin and glycerol or sucrose and gum arabic.

For topical administration to the epidermis, the compound can be formulated in the form of creams, gels, ointments or lotions, or in the form of a transdermal patch.

The compounds can also be formulated in the form of preparations for deposition. These formulations with a long lasting action can be administered by implantation (for example, subcutaneously or intramuscularly) or else by intramuscular injection. Thus, for example, the compounds can be formulated with suitable polymeric or hydrophobic materials (for example, in the form of an emulsion in an acceptable oil) or ion exchange resins, or in the form of very weakly soluble derivatives, for example in the form of a very weakly soluble salt.

For intranasal administration, the compounds of the present invention can be used, for example, in the form of an atomizing liquid, of a powder or of drops.

For administration by inhalation, the compounds in accordance with the present invention are suitably delivered in the form of an aerosol emitted by spraying with a pressurized container or a nebulizer, by means of a suitable propellant, for example 1,1,1,2-trifluoroethane (HFA 134A) and 1,1,1,2,3,3,3-heptafluoropropane (HFA 227), carbon dioxide or another suitable gas. In the case of a pressurized aerosol, the exact dose can be determined by installing a valve intended to deliver a measured amount. The capsules and cartridges consisting, for example, of gelatin, intended to be used in an inhaler or insufflation device can be formulated so as to contain a mixture of powders consisting of a compound of the present invention and a suitable powdered excipient such as lactose or starch.

In addition to the ingredients mentioned in particular above, the formulations can comprise other agents that are conventional in this field in relation to the type of formulation in question; for example, the formulations suitable for oral administration can comprise flavoring agents.

Those skilled in the art will note that a reference, in the present report, to a treatment extends to prophylaxis and also to the treatment of established diseases or symptoms. Furthermore, it will be noted that the amount of a compound of the present invention required for use in a treatment varies according to the nature of the condition treated and to the age and state of the patient, and will in the end be left to the discretion of the treating physician or veterinary. However, in general, the doses used for the treatment of an adult human patient are usually within the range of from 0.02 to 5000 mg per day, preferably from 1 to 1500 mg per day. The desired dose can be suitably provided in a single dose or fractionated in several doses administered at appropriate intervals, for example in the form of two, three, four or more than four secondary doses per day. The formulations in accordance with the present invention can contain 0.1 to 99% of the active ingredient, suitably 30 to 95% for tablets and capsules and 3 to 50% for liquid preparations.

The compound of formula (I) intended to be used in the present invention can be used in combination with one or more other therapeutic agents, for example beta-adrenergic receptor antagonists, calcium channel blockers, thiazide-type diuretics, angiotensin receptor antagonists and angiotensin-converting enzyme inhibitors. Thus, the present invention provides, in an additional aspect, the use of a combination comprising a compound of formula (I) and a supplementary therapeutic agent, in the treatment of arterial hypertension.

When the compounds of formula (I) are used in combination with other therapeutic agents, the compounds can be administered successively or simultaneously by any suitable route.

The combinations mentioned above can be suitably provided for use in the form of a pharmaceutical formulation and, thus, pharmaceutical formulations comprising a combination corresponding to the abovementioned definition together, optimally, with a pharmaceutically acceptable support or excipient constitute a supplementary aspect of the present invention. The various constituents of these combinations can be administered successively or simultaneously in separate or combined pharmaceutical formulations.

When they are combined in the same formulation, it will be noted that the two compounds must be stable and compatible with one another and the other constituents of the formulation, and can be formulated for administration. When they are formulated separately, they can be provided in any suitable formulation, conveniently in a known manner for such compounds in this field.

When a compound of formula (I) is used in combination with a second therapeutic agent that is active against the same disease, the dose of each compound can differ from that administered when the compound is used alone. The appropriate doses will be readily determined by those skilled in the art.

The compounds of formula (1) in which $R^1$ represents an alkyl group substituted with a group A which is an $SO_3H$ or $SO_3R'$ group and in which $R^2$ represents in particular an alkyl group substituted with a group B which can be a free or substituted phenyl group can be prepared by the following processes, the processes A and B being preferentially used.

These processes describe in particular the preparation of intermediate monomers for the synthesis of the disulfide compounds (or dimer compounds) of formula (1), which can be readily obtained by iodine oxidation.

These disulfide compounds are precursor compounds or "prodrugs", the dimeric structure of which facilitates crossing of the blood-brain barrier (BBB). The monomer, which is the active compound, is subsequently released by a physiological process (M. C. Fournié-Zaluski et al., *Proc. Natl. Acad. Sci. USA* 2004; 101, 7775-7780).

In process A, an olefination reaction allows conversion of the trimethyl ester of N-(benzyloxycarbonyl)-α-phosphonoglycine to dehydroamino acid 1 according to the method of U. Schmidt, H. Griesser, V. Leitenberger, A. Lieberknecht, R. Mangold, R. Meyer, B. Rield, *Synthesis*, 1992, 487-490. Compound 1 undergoes a Michael reaction so as to give a β-substituted cysteine 2 with an overall yield of 30 to 60%. A "one-pot" procedure makes it possible to obtain an α,β-unsaturated sulfonate 3 or an α,β-unsaturated phosphonate or carboxylate according to the method described by: C. David et al., *Tetrahedron*, 2000, 56, 209-215. Reduction of the compound 3 with sodium borohydride gives the compound 4. Deprotection of the compound 4 at the reflux of trifluoroacetic acid in the presence of anisole makes it possible, after precipitation, to isolate the compound 5, which can be readily converted to a disulfide (dimer compound 5) by oxidation with iodine.

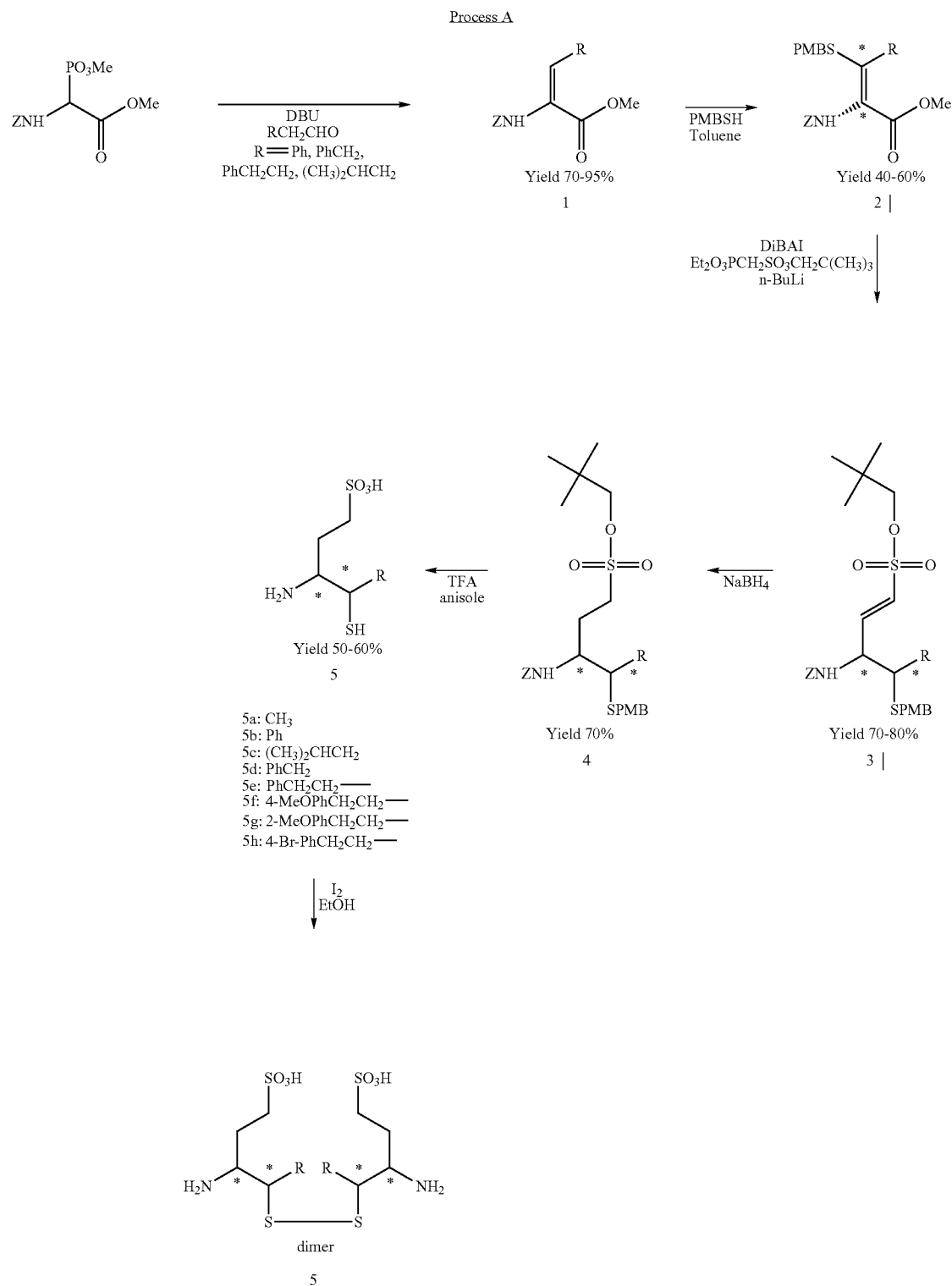

Z represents a suitable protective group, for example a benzyloxycarbonyl group.

With the aim of determining the stereochemical preferences of the compounds 5, a stereoselective synthesis of the four stereoisomers was carried out. This synthesis is based on the stereoselective production of β-substituted cysteines 2 according to the method of: C. Xiong, et al., *J. Org. Chem.*, 2002, 67, 3514-3517.

These syntheses are described in the schemes of processes B1-B4 hereinafter.
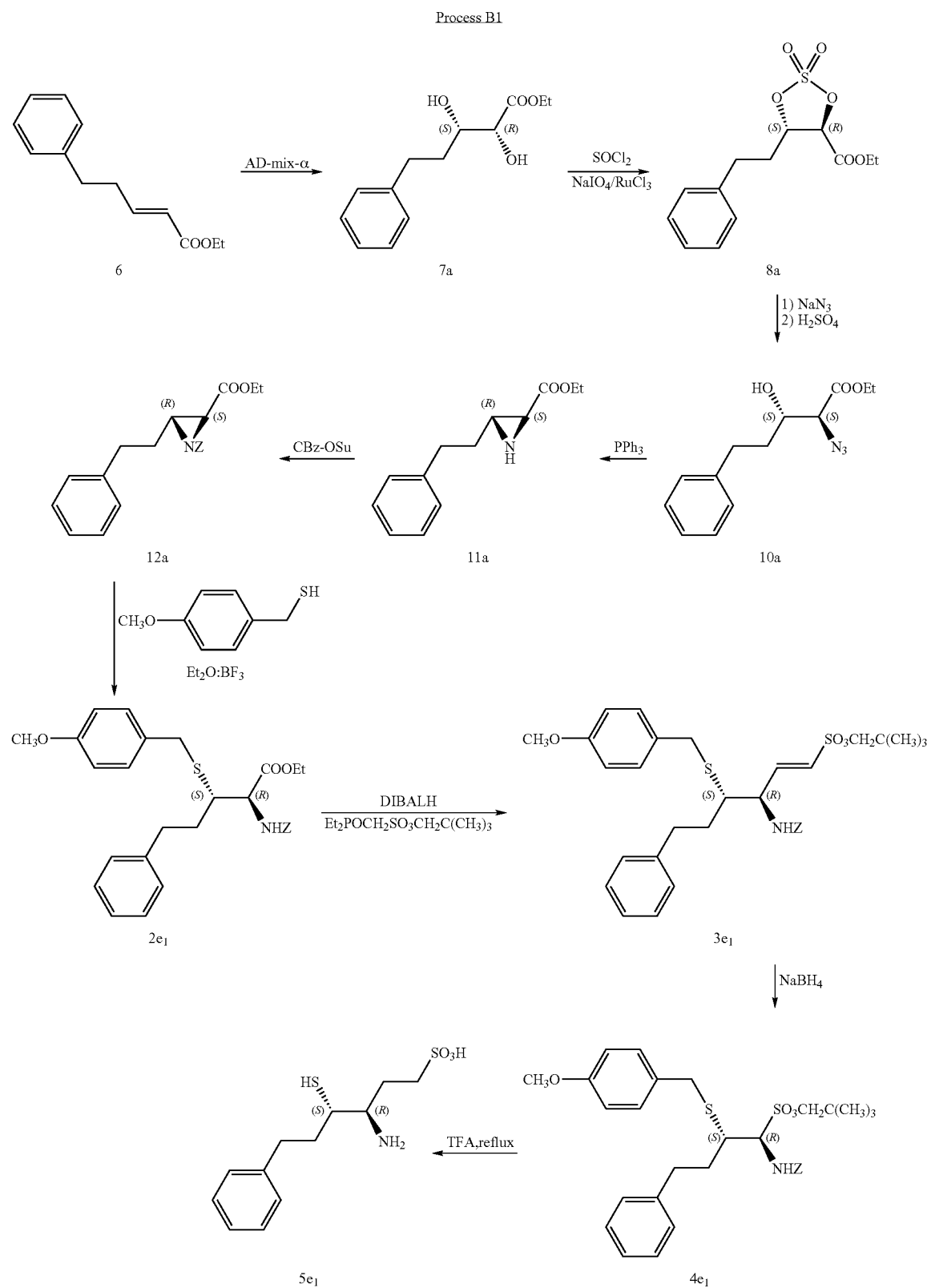

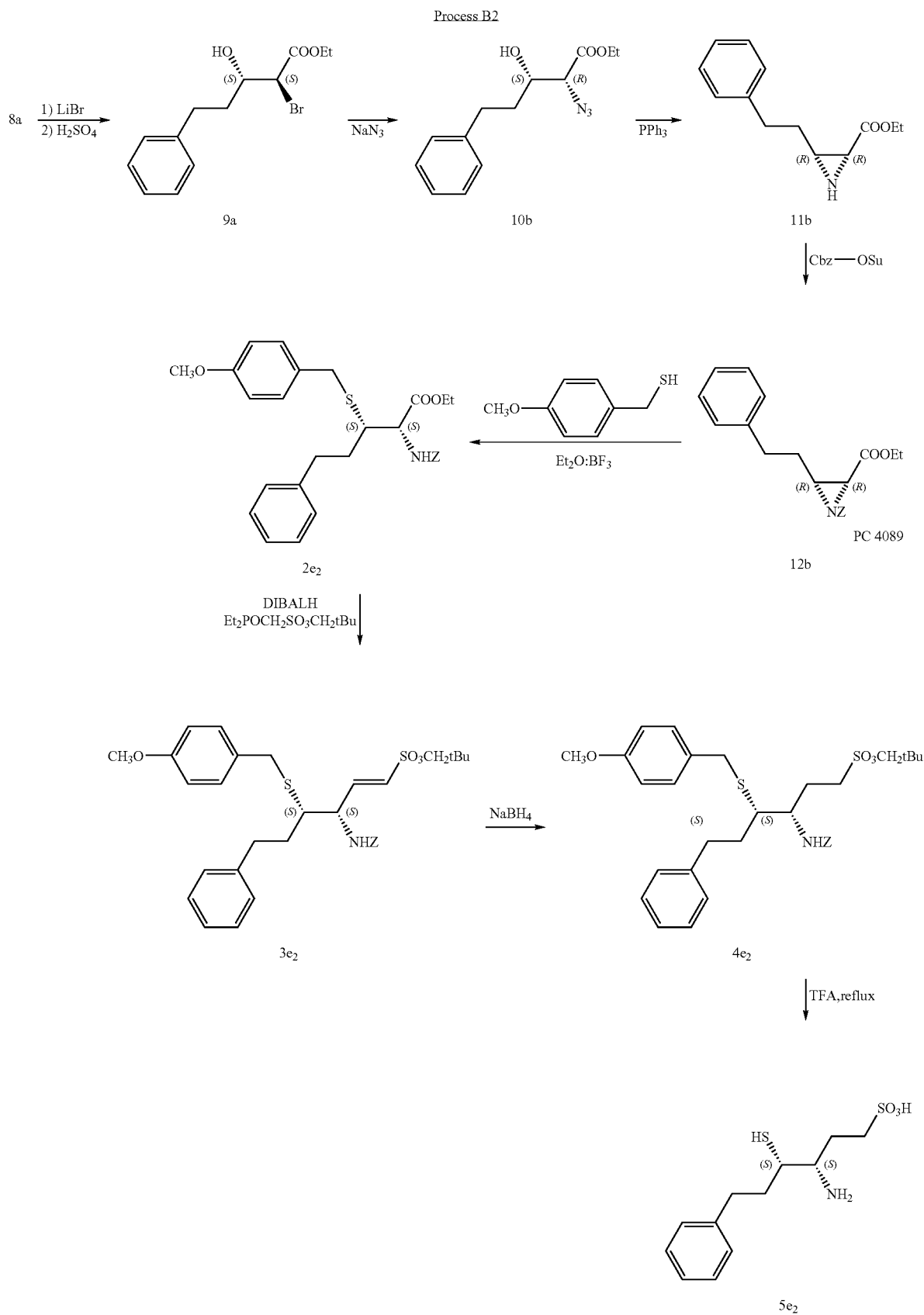

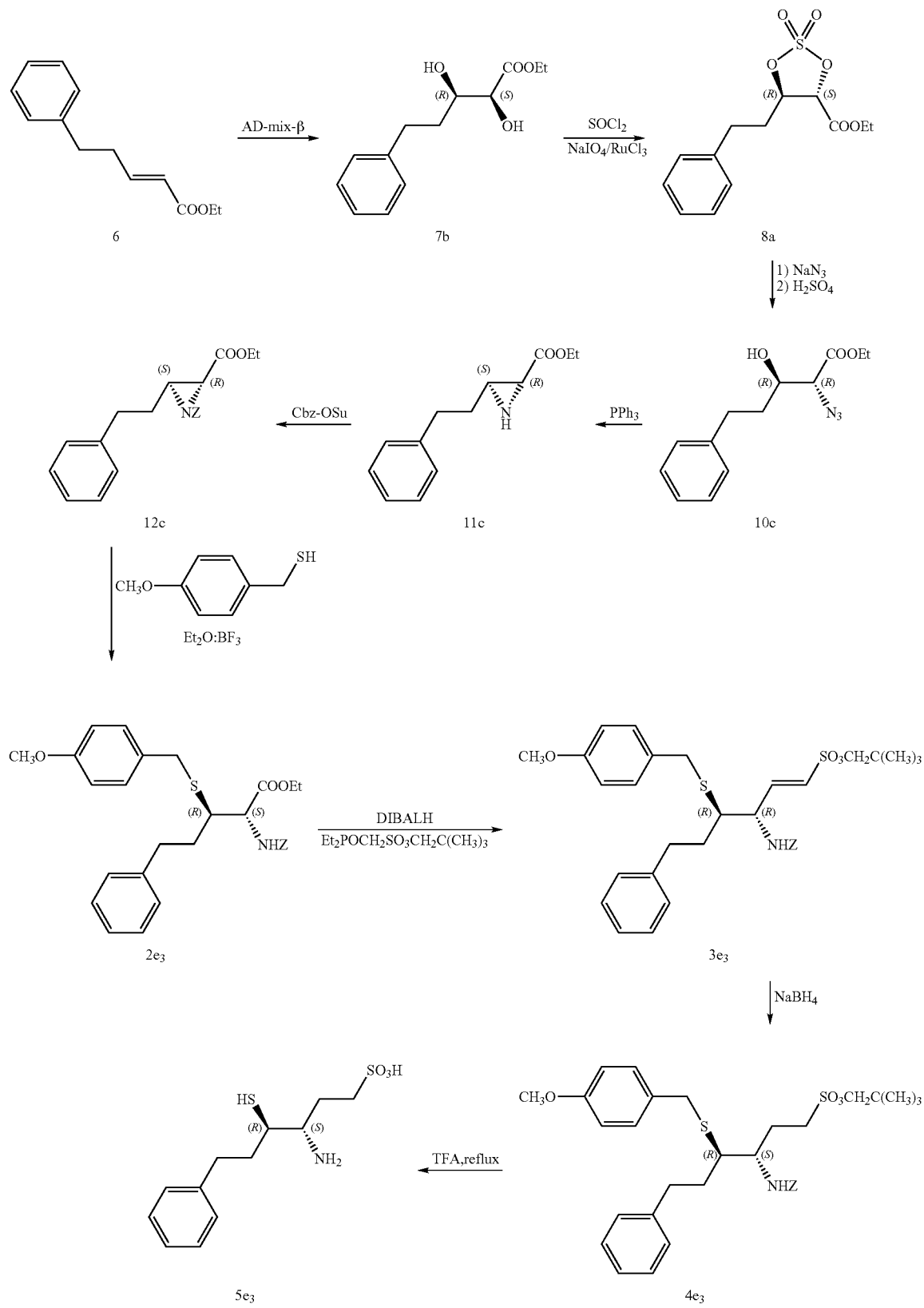
Process B3

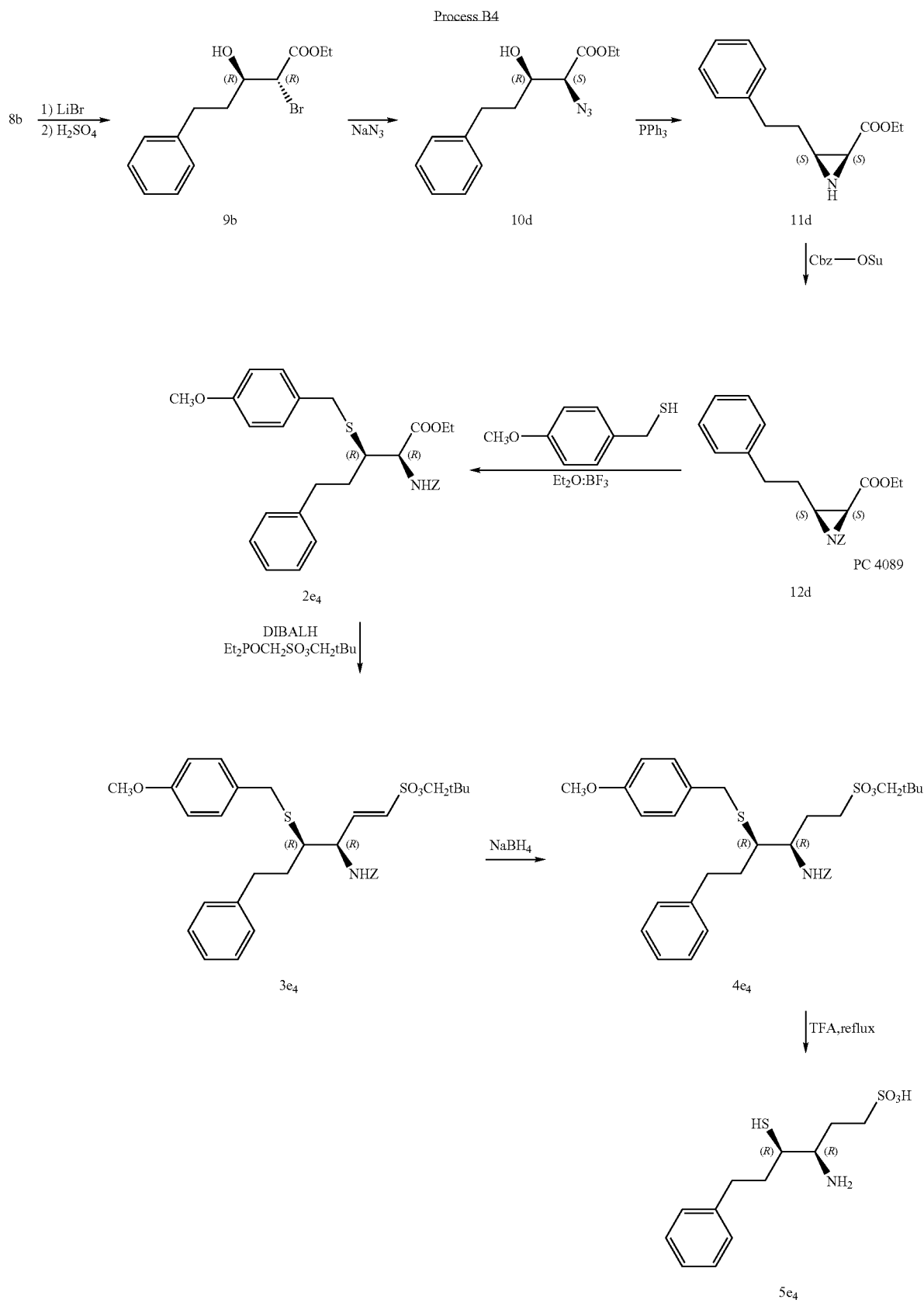

Other compounds of formula (1) can be prepared by processes similar to the processes above and will be evident to those skilled in the art, for instance the process illustrated by scheme 1 hereinafter.

Scheme 1

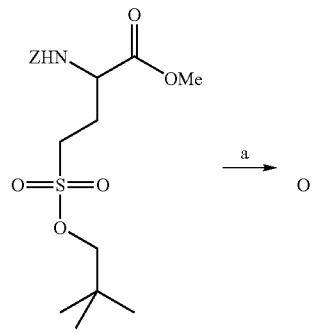

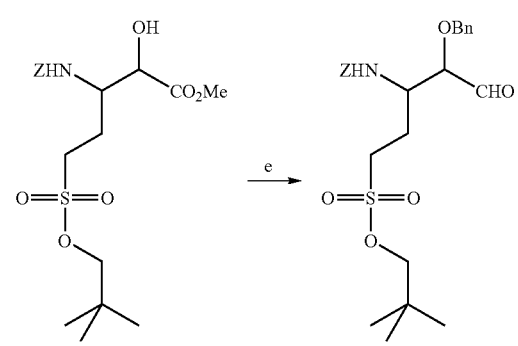

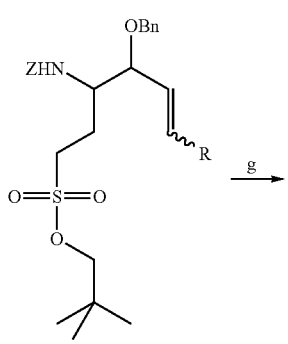

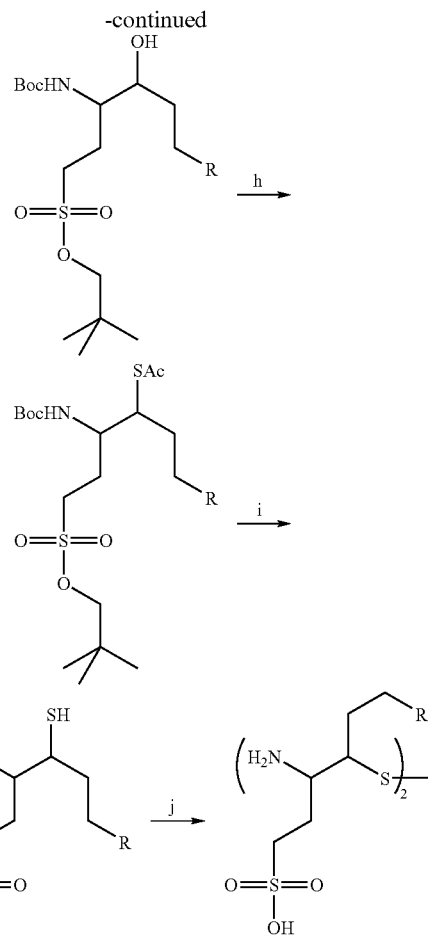

In Scheme 1, Z represents a suitable protective group, for example a benzyloxycarbonyl group, and the letters a to j represent the following conditions: a: $NaBH_4$, LiCl; b: DMSO, $(COCl_2)_2$; c: NaCN; d: HCl; MeOH; e: $PhCH_2Br$, NaH then DIBAL; f: $RCH_2PPH_3Br$, nBuLi; g: $H_2$, Pd/C, $Boc_2O$; h: Mitsunobu; i: HCl, reflux; j: $I_2$, EtOH.

The invention is illustrated in a nonlimiting manner by the following examples, in which the synthesis of the intermediate monomers that can be used in the synthesis of the compounds of formula (1) is described in the section "PREPARATIONS" and the numbers of the compounds refer to processes A and B described above.

Preparations

In the following preparations 1 to 5 (process A), the letters a to h refer to the compounds to which the variable R has the following definitions:

a R=$CH_3$ b R=Ph c R=$(CH_3)_2CHCH_2$— d R=$PhCH_2$— e R=$PhCH_2CH_2$— f R=4-$MeOPhCH_2CH_2$— g R=2-$MeOPhCH_2CH_2$— h R=4-$Br-PhCH_2CH_2$— with Ph=phenyl.

Preparations 6 to 16 refer to processes B1 to B4 described above

Preparation 1: Synthesis of the Compounds 1

0.76 ml (5 mmol) of diazabicycloundecene (DBU) is added, at 0° C., to a solution of N-benzyloxycarbonyl-α-phosphonoglycine methyl trimester 12 (5 mmol, 1.8 g) in 10 ml of dichloromethane. After 10 min, the aldehyde (5 mmol) is added. The reaction mixture is stirred at ambient temperature overnight. The reaction mixture is dissolved with 30 ml of dichloromethane, and subsequently washed with 2×10 ml, then with 2×10 ml of a saturated sodium chloride solution. The organic phase is dried over sodium sulfate and then concentrated under reduced pressure, and the oil obtained is purified by filtration over silica (20 g), elution being carried out with 9/1 cyclohexane/ethyl acetate.

The compounds 1a, 1b, 1c, 1d, 1e, 1f, 1g and 1h were obtained in the same manner and were characterized by means of their $^1$H NMR spectrum in CDCl$_3$ at 400 MHz.

Compound 1a:

Methyl (2Z)-2-(N-benzyloxycarbonylamino)but-2-enoate

Yield 72%. $^1$H NMR (CDCl$_3$): 1.85 (d, 3H, J=7 Hz, CH$_3$), 3.75 (s, 3H, CH$_3$O), 5.15 (s, 2H, O—CH$_2$—C$_6$H$_5$), 6.2 (s, 1H, NH), 6.78 (q, 1H, J=7 Hz, CH=C), 7.43 (m, 5H, O—CH$_2$—C$_6$H$_5$).

Compound 1b

Methyl (2Z)-2-(N-benzyloxycarbonylamino)-3-phenylpro-2-enoate

Yield 55%. $^1$H NMR (CDCl$_3$): 3.75 (s, 3H, CH$_3$O), 5.15 (s, 2H, O—CH$_2$—C$_6$H$_5$), 6.4 (s, 1H, NH), 7.43 (m, 5H, O—CH$_2$—C$_6$H$_5$), 7.52 (d, 1H, J=3 Hz, CH=C).

Compound 1c

Methyl (2Z)-2-(N-benzyloxycarbonylamino)-5-methylhex-2-enoate

Yield 95%. $^1$H NMR (CDCl$_3$): 0.95 (d, 6H, J=7 Hz, CH—CH$_3$), 1.8 (hpt, 1H, J=7 Hz, CH—CH$_3$), 2.1 (t, 2H, J=7 Hz, CH—CH$_2$), 3.75 (s, 3H, CH$_3$O), 5.15 (s, 2H, O—CH$_2$—C$_6$H$_5$), 6.15 (s, 1H, NH), 6.78 (q, 1H, J=7 Hz, CH=C), 7.43 (m, 5H, O—CH$_2$—C$_6$H$_5$).

Compound 1d

Methyl (2Z)-2-(N-benzyloxycarbonylamino)-4-phenylbut-2-enoate

Yield 82%. $^1$H NMR (CDCl$_3$): 3.57 (d, 2H, J=7 Hz, CH—CH$_2$—C$_6$H$_5$), 3.75 (s, 3H, CH$_3$O), 5.15 (s, 2H, O—CH$_2$—C$_6$H$_5$), 6.3 (s, 1H, NH), 6.78 (q, 1H, J=7 Hz, CH=C), 7.2-7.3 (m, 5H, CH$_2$—C$_6$H$_5$), 7.43 (m, 5H, O—CH$_2$—C$_6$H$_5$).

Compound 1e

Ethyl (2Z)-2-(N-benzyloxycarbonylamino)-5-phenylpent-2-enoate

Yield 100%. $^1$H NMR (CDCl$_3$): 2.52 (q, 2H, J=7 Hz, CH$_2$—CH$_2$—CH), 2.80 (t, 2H, J=7 Hz, CH$_2$—CH$_2$—CH), 3.75 (s, 3H, CH$_3$O), 5.15 (s, 2H, O—CH$_2$—C$_6$H$_5$), 6.1 (s, 1H, NH), 6.68 (t, 1H, J=7 Hz, CH=C), 7.2 (m, 2H, CH$_2$—C$_6$H$_5$), 7.3 (m, 3H, CH$_2$—C$_6$H$_5$), 7.43 (m, 5H, O—CH$_2$C$_6$H$_5$).

Compound 1f

Ethyl (2Z)-2-(N-benzyloxycarbonylamino)-5-(4-methoxyphenyl)pent-2-enoate

Yield 80%. $^1$H NMR (CDCl$_3$): 2.51 (q, 2H, J=7 Hz, CH$_2$—CH$_2$—CH), 2.72 (t, 2H, J=7 Hz, CH$_2$—CH$_2$—CH), 3.75 (s, 3H, CO$_2$CH$_3$), 3.8 (s, 3H, CH$_3$O), 5.15 (s, 2H, O—CH$_2$—C$_6$H$_5$), 6.1 (s, 1H, NH), 6.65 (t, 1H, J=7 Hz, CH=C), 6.8 (d, 2H, 4-CH$_3$O—C$_6$H$_4$), 7.1 (d, 2H, 4-CH$_3$—C$_6$H$_4$), 7.3-7.4 (5H, m, CH$_2$—C$_6$H$_5$).

Compound 1g

Ethyl (2Z)-2-(N-benzyloxycarbonylamino)-5-(2-methoxyphenyl)pent-2-enoate

Yield 61%. $^1$H NMR (CDCl$_3$): 2.5 (m, 2H, CH$_2$—CH$_2$—CH), 2.75 (t, 2H, J=7 Hz, CH$_2$—CH$_2$—CH), 3.75 (s, 3H, CO$_2$CH$_3$), 3.8 (s, 3H, CH$_3$O), 5.15 (s, 2H, O—CH$_2$—C$_6$H$_5$), 6.1 (s, 1H, NH), 6.7 (t, 1H, J=7 Hz, CH=C), 6.85 (d, 1H, 2-CH$_3$O—C$_6$H$_4$), 6.9 (dd, 1H, 2-CH$_3$—O—C$_6$H$_4$), 7.1 (d, 1H, 2-CH$_3$O—C$_6$H$_4$), 7.2 (t, 1H, 2-CH$_3$O—C$_6$H$_4$), 7.3-7.4 (5H, m, CH$_2$—C$_6$H$_5$).

Compound 1h

Ethyl (2Z)-2-(N-benzyloxycarbonylamino)-5-(4-bromophenyl)pent-2-enoate

Yield 41%. $^1$H NMR (CDCl$_3$): 2.51 (q, 2H, J=7 Hz, CH$_2$—CH$_2$—CH), 2.72 (t, 2H, J=7 Hz, CH$_2$—CH$_2$—CH), 3.75 (s, 3H, CO$_2$CH$_3$), 5.15 (s, 2H, O—CH$_2$—C$_6$H$_5$), 6.1 (s, 1H, NH), 6.65 (t, 1H, J=7 Hz, CH=C), 7.0 (d, 2H, 4-Br—C$_6$H$_4$), 7.3-7.4 (5H, m, CH$_2$—C$_6$H$_5$), 7.5 (d, 2H, 4-Br—C$_6$H$_4$).

Preparation 2: Synthesis of the Compounds 2

200 μl of piperidine are added to a solution of 1 (5 mmol) and of 4-methoxybenzylmercaptan (10 mmol) in 10 ml of anhydrous toluene. The mixture is brought to reflux for 24 h under argon. The solvent is eliminated under reduced pressure. After purification by column chromatography (eluent, dichloromethane), an oil is obtained.

The compounds 2a, 2b, 2c, 2d, 2e, 2f, 2g and 2h were obtained in the same manner and were characterized by means of their $^1$H NMR spectrum in CDCl$_3$ at 400 MHz.

Compound 2a

Methyl 2-benzyloxycarbonylamino-3-(4-methoxybenzylsulfanyl)butyrate

Yield 73%, HPLC (80%): Tr=5.2 and 5.4 min $^1$H NMR (CDCl$_3$): 1.2 and 1.3 (d, 3H, J=7 Hz, CH$_3$), 3.1 and 3.3 (m, 1H, —CH—S), 3.6, 3.65, 3.7 and 3.75 (s, 8H, CO$_2$CH$_3$, S—CH2, CH$_3$O), 4.5 and 4.6 (dd, 1H, CH—CO$_2$), 5.15 (s, 2H, O—CH$_2$—C$_6$H$_5$), 5.4 and 5.55 (d, 1H, NH), 6.2 (s, 1H, NH), 6.78 (d, 2H, J=7 Hz, S—C$_6$H$_4$), 7.2 (d, 2H, J=7 Hz, S—C$_6$H$_4$), 7.43 (m, 5H, O—CH$_2$C$_6$H$_5$).

Compound 2b

Methyl 2-benzyloxycarbonylamino-3-(4-methoxybenzylsulfanyl)-3-phenylpropanoate

Yield 60%. HPLC (80%): Tr=6.7 min. $^1$H NMR (CDCl$_3$): 3.5 and 3.6 (s, 2H, —CH$_2$—S), 3.6 (s, 3H, CH$_3$O), 3.75 (s, 3H, CO$_2$CH$_3$), 4.1 and 4.15 (d, 1H, J=4 Hz, —CH—S), 4.65 and 4.85 (dd, 1H, CH—CO$_2$), 5.15 (s, 2H, O—CH$_2$—C$_6$H$_5$), 5.2 and 5.45 (d, 1H, NH), 6.75 (d, 2H, J=7 Hz, S—C$_6$H$_4$), 7.05 and 7.1 (d, 2H, J=7 Hz, S—C$_6$H$_4$), 7.43 (m, 10H, O—CH$_2$—C$_6$H$_5$ and CH—C$_6$H$_5$).

Compound 2c

Methyl 2-benzyloxycarbonylamino-3-(4-methoxybenzylsulfanyl)-5-methylhexenoate

Yield 33%. HPLC (80%): Tr=8.3 and 9.3 min. $^1$H NMR (CDCl$_3$): 0.65 and 0.7 (d, 3H, CH—CH$_3$), 0.8 (d, 3H, CH—CH$_3$), 1.2-1.4 (m, 2H, CH$_2$—CH), 1.7 (m, 1H, CH—CH$_3$), 2.9 and 3.2 (m, 1H, —CH—S), 3.55 (s, 2H, —CH$_2$—S), 3.7 (s, 3H, CH$_3$O), 3.75 (s, 3H, CO$_2$CH$_3$), 4.6 and 4.65 (dd, 1H, CH—CO$_2$), 5.15 (s, 2H, O—CH$_2$—C$_6$H$_5$), 5.45 and 5.55 (d, 1H, NH), 6.75 (d, 2H, J=7 Hz, S—C$_6$H$_4$), 7.05 and 7.1 (d, 2H, J=7 Hz, S—C$_6$H$_4$), 7.43 (m, 5H, O—CH$_2$—C$_6$H$_5$).

Compound 2d

Methyl 2-benzyloxycarbonylamino-3-(4-methoxybenzylsulfanyl)-4-phenylbutyrate

Yield 45%. HPLC (80%): Tr=8.0 and 8.4 min. $^1$H NMR (CDCl$_3$): 2.8, 2.90 and 3.05 (dd, 2H, S—CH—CH$_2$), 3.4 (m, 1H, S—CH—CH$_2$), 3.55 (s, 3H, CH$_3$O), 3.6 and 3.75 (s, 2H, —CH$_2$—S), 3.8 (s, 3H, CO$_2$CH$_3$), 4.55 (dd, 1H, CH—CO$_2$), 5.05 and 5.15 (s, 2H, O—CH$_2$—C$_6$H$_5$), 5.5 (d, 1H, NH), 6.75 (d, 2H, J=7 Hz, S—C$_6$H$_4$), 7.05 (d, 2H, J=7 Hz, S—C$_6$H$_4$), 7.1-7.43 (m, 10H, O—CH$_2$—C$_6$H$_5$ and CH$_2$—C$_6$H$_5$).

Compound 2e

Methyl 2-benzyloxycarbonylamino-3-(4-methoxybenzylsulfanyl)-5-phenylpentanoate

Yield 84%. HPLC (80%): Tr=8.3 and 9.1 min. $^1$H NMR (CDCl$_3$): 1.7-2.0 (m, 2H, CH—CH$_2$—CH$_2$), 2.5-2.75 (m, 2H, CH—CH$_2$—CH$_2$), 2.8 and 3.1 (m, 1H, S—CH—CH$_2$), 3.55 and 3.65 (s, 2H, —CH$_2$—S), 3.7 (s, 3H, CH$_3$O), 3.8 (s, 3H, CO$_2$CH$_3$), 4.6 and 4.7 (dd, 1H, CH—CO$_2$), 5.15 (s, 2H, O—CH$_2$—C$_6$H$_5$), 5.4 and 5.6 (d, 1H, NH), 6.80 (d, 2H, J=7 Hz, S—C$_6$H$_4$), 7.0 and 7.1 (d, 2H, J=7 Hz, S—C$_6$H$_4$), 7.2-7.43 (m, 10H, O—CH$_2$—C$_6$H$_5$ and CH$_2$—C$_6$H$_5$).

Compound 2f

Methyl 2-benzyloxycarbonylamino-3-(4-methoxybenzylsulfanyl)-5-(4-methoxyphenyl)pentanoate Yield 71%. HPLC (80%): Tr=7.9 and 8.4 min. $^1$H NMR (CDCl$_3$): 1.7-1.9 (m, 2H, CH—CH$_2$—CH$_2$), 2.45 and 2.83 (m, 2H, CH—CH$_2$—CH$_2$), 2.86 and 3.1 (m, 1H, S—CH—CH$_2$), 3.55 and 3.65 (s, 2H, —CH$_2$—S), 3.7 (s, 3H, CH$_3$O), 3.8 (m, 6H, CO$_2$CH$_3$ and CH$_3$O), 4.65-4.7 (dd, 1H, CH—CO$_2$), 5.13 (s, 2H, O—CH$_2$—C$_6$H$_5$), 5.45 and 5.53 (d, 1H, NH), 6.8 (m, 4H, H Aromatic), 6.9-7.2 (m, 4H, H Aromatic), 7.3-7.4 (m, 5H, CH$_2$—C$_6$H$_5$).

Compound 2g

Methyl 2-benzyloxycarbonylamino-3-(4-methoxybenzylsulfanyl)-5-(2-methoxyphenyl)pentanoate Yield 62%. HPLC (80%): Tr=8.9 and 9.6 min. $^1$H NMR (CDCl$_3$): 1.7-1.9 (m, 2H, CH—CH$_2$—CH$_2$), 2.56 and 2.83 (m, 2H, CH—CH$_2$—CH$_2$), 2.86 and 3.1 (m, 1H, S—CH—CH$_2$), 3.55 and 3.7 (s, 2H, —CH$_2$—S), 3.63 and 3.66 (s, 3H, CH$_3$O), 3.8 (s, 6H, CO$_2$CH$_3$ and CH$_3$O), 4.66 and 4.76 (dd, 1H, CH—CO$_2$), 5.13 (s, 2H, O—CH$_2$—C$_6$H$_6$), 5.45 and 5.53 (d, 1H, NH), 6.76-6.95 (m, 4H, H Aromatic), 7.03 (m, 1H, H Aromatic), 7.06 (d, 1H, H Aromatic), 7.15-7.25 (m, 2H, H Aromatic), 7.3-7.4 (m, 5H, CH$_2$—C$_6$H$_5$).

Compound 2h

Methyl 2-benzyloxycarbonylamino-3-(4-methoxybenzylsulfanyl)-5-(4-bromophenyl)pentanoate Yield 57%. HPLC (80%): Tr=15.1 and 15.9 min. $^1$H NMR (CDCl$_3$): 1.6-1.8 (m, 2H, CH—CH$_2$—CH$_2$), 2.5-2.7 (m, 2H, CH—CH$_2$—CH$_2$), 2.8 and 3.1 (m, 1H, S—CH—CH$_2$), 3.55 and 3.65 (s, 2H, —CH$_2$—S), 3.7 (s, 3H, CH$_3$O), 3.8 (m, 3H, CO$_2$CH$_3$), 4.6-4.7 (dd, 1H, CH—CO$_2$), 5.13 (s, 2H, O—CH$_2$—C$_6$H$_5$), 5.45 and 5.6 (d, 1H, NH), 6.6-6.8 (m, 4H, H Aromatic), 7.1-7.2 (m, 4H, H Aromatic), 7.3-7.4 (m, 5H, CH$_2$—C$_6$H$_5$).

Preparation 3: Synthesis of the Compounds 3

A 1.6M solution of n-butyllithium in hexane (2 equivalents) is added dropwise, at –78° C., to a solution of neopentyl diethoxyphosphorylmethanesulfonate (2 equivalents) in anhydrous THF (4.5 ml/mmol). After 30 min with stirring, a solution of compound 2 (1 equivalent) in anhydrous THF (1 ml/mmol) is added, followed by the introduction, dropwise, of a 1.6M solution of diisobutylaluminum hydride in toluene (2 equivalents). The reaction mixture is maintained at –78° C. for 4 h, and the temperature is then allowed to return to ambient temperature overnight. The solvents are eliminated under reduced pressure, and 10 ml/mmol of ether and 5 ml/mmol of 2N HCl are added to the residue. The mixture is stirred for 30 min, the organic phase is separated, and the aqueous phase is extracted twice with an equivalent volume of ether. The organic phases are combined, dried over Na$_2$SO$_4$ and concentrated under reduced pressure. The oil obtained is purified by silica chromatography. After elimination of the solvents, product 3 is obtained in the form of an oil.

The compounds 3a, 3b, 3c, 3d, 3e, 3f, 3g and 3h are obtained in the same manner and are characterized by means of their $^1$H NMR spectrum in CDCl$_3$ at 400 MHz.

Compound 3a 2,2-Dimethylpropyl 3-benzyloxycarbonylamino-4-(4-methoxybenzylsulfanyl)pent-1-ene-1-sulfonate Yield 42%. HPLC (80%): Tr=8.1 and 8.4 min. $^1$H NMR (CDCl$_3$): 1.0 (s, 9H, C(CH$_3$)$_3$), 1.2 and 1.3 (d, 3H, J=7 Hz, CH$_3$), 2.8 (m, 1H, —CH—S), 3.6-3.9 (m, 7H, SO$_3$CH$_2$, S—CH$_2$, CH$_3$O), 4.6 (m, 1H, CH—N), 5.15 (s, 2H, O—CH$_2$—C$_6$H$_5$), 5.2 (d, 1H, NH), 6.3 (d, 1H, CH=CH—SO$_3$), 6.7 (dd, 1H, CH=CH—SO$_3$), 6.8 (m, 2H, S—C$_6$H$_4$), 7.2 (m, 2H, S—C$_6$H$_4$), 7.43 (m, 5H, O—CH$_2$—C$_6$H$_5$).

Compound 3b 2,2-Dimethylpropyl 3-benzyloxycarbonylamino-4-(4-methoxybenzylsulfanyl)-4-phenylbut-1-ene-1-sulfonate Yield 42%. HPLC (80%): Tr=10.8 min. $^1$H NMR (CDCl$_3$): 0.9 (s, 9H, C(CH$_3$)$_3$), 3.4 (m, 2H, S—CH$_2$), 3.6 (s, 2H, SO$_3$CH$_2$), 3.8 (s, 3H, CH$_3$O), 3.9 (m, 1H, —CH—S), 4.8 (m, 1H, CH—N), 5.05 (s, 2H, O—CH$_2$—C$_6$H$_5$), 5.1 (d, 1H, NH), 6.1 (d, 1H, CH=CH—SO$_3$), 6.7 (dd, 1H, CH=CH—SO$_3$), 6.8 (m, 2H, S—C$_6$H$_4$), 7.2 (m, 2H, S—C$_6$H$_4$), 7.43 (m, 10H, H aromatic).

Compound 3c

2,2-Dimethylpropyl 3-benzyloxycarbonylamino-4-(4-methoxybenzylsulfanyl)-6-methylhept-1-ene-1-sulfonate Yield 56%. HPLC (80%): Tr=14.4 and 15.4 min. $^1$H NMR (CDCl$_3$): 0.6 and 0.8 (d, 6H, J=7 Hz, CH(CH$_3$)$_2$), 0.9 (s, 9H, C(CH$_3$)$_3$), 1.2-1.4 (m, 2H, CH$_2$—CH), 1.7 (m, 1H, CH(CH$_3$)$_2$), 2.7 (m, 1H, —CH—S), 3.6-3.9 (m, 7H, SO$_3$CH$_2$, S—CH$_2$, CH$_3$O), 4.6 (m, 1H, CH—N), 5.05 (s, 2H, O—CH$_2$—C$_6$H$_5$), 5.1 (d, 1H, NH), 6.3 (d, 1H, CH=CH—SO$_3$), 6.7 (dd, 1H, CH=CH—SO$_3$), 6.8 (m, 2H, S—C$_6$H$_4$), 7.2 (m, 2H, S—C$_6$H$_4$), 7.43 (m, 5H, H aromatic).

Compound 3d

2,2-Dimethylpropyl 3-benzyloxycarbonylamino-4-(4-methoxybenzylsulfanyl)-5-phenylpent-1-ene-1-sulfonate Yield 76%. HPLC (80%): Tr=12.7 min. $^1$H NMR (CDCl$_3$): 0.9 (s, 9H, C(CH$_3$)$_3$), 2.8 (m, 3H, CH$_2$—CH—S), 3.6-3.9 (m, 7H, SO$_3$CH$_2$, S—CH$_2$, CH$_3$O), 4.6 (m, 1H, CH—N), 5.05 (s, 2H, O—CH$_2$—C$_6$H$_5$), 5.1 (d, 1H, NH), 6.3 (d, 1H, CH=CH—SO$_3$), 6.7 (dd, 1H, CH=CH—SO$_3$), 6.8 (m, 2H, S—C$_6$H$_4$), 7.0 (m, 2H, H aromatic), 7.2 (m, 2H, S—C$_6$H$_4$), 7.43 (m, 8H, H aromatic).

Compound 3e

2,2-Dimethylpropyl 3-benzyloxycarbonylamino-4-(4-methoxybenzylsulfanyl)-6-phenylhex-1-ene-1-sulfonate Yield 74%. HPLC (80%): Tr=15.1 and 16.0 min. $^1$H NMR (CDCl$_3$): 0.9 (S, 9H, C(CH$_3$)$_3$), 1.8 (m, 2H, CH$_2$—CH—S), 2.6 (m, 2H, CH$_2$—CH$_2$—CH—S), 2.8 (m, 1H, CH—S), 3.6-3.9 (m, 7H, SO$_3$CH$_2$, S—CH$_2$, CH$_3$O), 4.6-4.7 (m, 1H, CH—N), 5.05 and 5.2 (d, 1H, NH), 5.15 (s, 2H, O—CH$_2$—C$_6$H$_5$), 6.3 (d, 1H, CH=CH—SO$_3$), 6.7 (dd, 1H, CH=CH—SO$_3$), 6.8 (m, 2H, S—C$_6$H$_4$), 7.0-7.1 (m, 5H, H aromatic), 7.2 (m, 2H, S—C$_6$H$_4$), 7.43 (m, 5H, H aromatic).

Compound 3f

2,2-Dimethylpropyl 3-benzyloxycarbonylamino-4-(4-methoxybenzylsulfanyl)-6-(4-methoxyphenyl)hex-1-ene-1-sulfonate Yield 59%. HPLC (80%): Tr=13.2 and 14.0 min. $^1$H NMR (CDCl$_3$): 0.9 (S, 9H, C(CH$_3$)$_3$), 1.8 (m, 2H, CH$_2$—CH—S), 2.6 (m, 2H, CH$_2$—CH$_2$—CH—S), 2.8 (m, 1H, CH—S), 3.6-3.9 (m, 10H, SO$_3$CH$_2$, S—CH$_2$, CH$_3$O), 4.6-4.7 (m, 1H, CH—N), 5.05 and 5.2 (d, 1H, NH), 5.15 (s, 2H, O—CH$_2$—C$_6$H$_5$), 6.3 (d, 1H, CH=CH—SO$_3$), 6.7 (dd, 1H, CH=CH—SO$_3$), 6.8 (m, 4H, H aromatic), 7.2 (m, 4H, H aromatic), 7.43 (m, 5H, H aromatic).

Compound 3g

2,2-Dimethylpropyl 3-benzyloxycarbonylamino-4-(4-methoxybenzylsulfanyl)-6-(2-methoxyphenyl)hex-1-ene-1-sulfonate Yield 62%. HPLC (80% B): Tr=15.74 and 16.17 min. $^1$H NMR (CDCl$_3$): 1 (s, 9H, C(CH$_3$)$_3$), 1.8 (m, 2H, CH$_2$—CH—S), 2.6 (m, 2H, CH$_2$—CH$_2$—CH—S), 2.8 (m, 1H, CH—S), 3.6-3.8 (m, 10H, SO$_3$CH$_2$, S—CH$_2$, CH$_3$O), 4.7-4.8 (m, 1H, CH—N), 5.15 (m, 2H, O—CH$_2$—C$_6$H$_5$), 5.2 (d, 1H, NH), 6.3 (d, 1H, CH=CH—SO$_3$), 6.7 (dd, 1H, CH=CH—SO$_3$), 6.8 (m, 2H, H aromatic), 7.03-7.25 (m, 4H, H aromatic), 7.43 (m, 7H, H aromatic).

Compound 3h

2,2-Dimethylpropyl 3-benzyloxycarbonylamino-4-(4-methoxybenzylsulfanyl)-6-(4-bromophenyl)hex-1-ene-1-sulfonate Yield 45%. HPLC (80%): Tr=21.8 and 23.3 min. $^1$H NMR (CDCl$_3$): 0.9 (s, 9H, C(CH$_3$)$_3$), 1.8 (m, 2H, CH$_2$—CH—S), 2.6 (m, 2H, CH$_2$—CH$_2$—CH—S), 2.8 (m, 1H, CH—S), 3.6-3.9 (m, 7H, SO$_3$CH$_2$, S—CH$_2$, CH$_3$O), 4.6-4.7 (m, 1H, CH—N), 5.2 (d, 1H, NH), 5.15 (m, 2H, O—CH$_2$—C$_6$H$_5$), 6.3 (d, 1H, CH=CH—SO$_3$), 6.7 (dd, 1H, CH=CH—SO$_3$), 6.8 (m, 2H, H aromatic), 6.9-7.2 (m, 4H, H aromatic), 7.43 (m, 7H, H aromatic).

Preparation 4: Synthesis of the Compounds 4

Sodium borohydride (1 equivalent) is added to a solution of a compound 3 (1 equivalent) in absolute ethanol (5 ml/mmol). The reaction mixture is stirred at ambient temperature overnight. The solvents are eliminated under reduced pressure, and 10 ml/mmol of ethyl acetate and 5 ml/mmol of water are added to the residue. The organic phase is separated, and the aqueous phase is extracted twice with an equivalent volume of ethyl acetate. The organic phases are combined, dried over Na$_2$SO$_4$ and concentrated under reduced pressure. The oil obtained is purified by semi-preparative HPLC. After elimination of the solvents, product 16 is obtained in the form of an oil.

The compounds 4a, 4b, 4c, 4d, 4e, 4f, 4g and 4h were obtained in the same manner and were characterized by means of their $^1$H NMR spectrum in CDCl$_3$ at 400 MHz and by electrospray mass spectroscopy.

Compound 4a

2,2-Dimethylpropyl 3-benzyloxycarbonylamino-4-(4-methoxybenzylsulfanyl)pentane-1-sulfonate Yield 30%. HPLC (80%): Tr=7.5 and 7.7 min. $^1$H NMR (CDCl$_3$): 1.0 (s, 9H, C(CH$_3$)$_3$), 1.2 and 1.3 (d, 3H, J=7 Hz, CH$_3$), 1.8-2.1 (m, 2H, CH$_2$CH$_2$—SO$_3$), 2.8 (m, 1H, —CH—S), 3.0 (m, 2H, CH$_2$—CH$_2$—SO$_3$), 3.6-3.9 (m, 8H, SO$_3$CH$_2$, CH—S—CH$_2$, CH$_3$O), 4.7-5.0 (d, 1H, NH), 5.15 (m, 2H, O—CH$_2$—C$_6$H$_5$), 6.8 (m, 2H, S—C$_6$H$_4$), 7.2 (m, 2H, S—C$_6$H$_4$), 7.43 (m, 5H, O—CH$_2$—C$_6$H$_5$). ES$^+$: 546 M+Na$^+$.

Compound 4b

2,2-Dimethylpropyl 3-benzyloxycarbonylamino-4-(4-methoxybenzylsulfanyl)-4-phenylbutane-1-sulfonate Yield 62%. HPLC (80%): Tr=10.3 min. $^1$H NMR (CDCl$_3$): 1.0 (s, 9H, C(CH$_3$)$_3$), 1.8 (m, 1H, CH$_2$CH$_2$—SO$_3$), 2.1 (m, 1H, CH$_2$CH$_2$—SO$_3$), 3.2 (m, 2H, CH$_2$—CH$_2$—SO$_3$), 3.4 (m, 1H, —CH—S), 3.7-3.8 (m, 7H, SO$_3$CH$_2$, S—CH$_2$, CH$_3$O), 4.05 (m, 1H, CH—S), 4.8 (d, 1H, NH), 5.15 (m, 2H, O—CH$_2$—C$_6$H$_5$), 6.8 (m, 2H, S—C$_6$H$_4$), 7.05 (m, 2H, S—C$_6$H$_4$), 7.43 (m, 10H, H aromatic). ES$^+$: 608 M+Na$^+$.

Compound 4c 2,2-Dimethylpropyl 3-benzyloxycarbonylamino-4-(4-methoxybenzylsulfanyl)-6-methylheptane-1-sulfonate Yield 80%. HPLC (80%): Tr=13.8 and 14.5 min. $^1$H NMR (CDCl$_3$): 0.6 and 0.8 (d, 6H, J=7 Hz, CH(CH$_3$)$_2$), 0.9 (s, 9H, C(CH$_3$)$_3$), 1.2-1.4 (m, 2H, CH$_2$—CH), 1.6-1.8 (m, 2H, CH$_2$CH$_2$—SO$_3$), 2.0 (m, 1H, CH(CH$_3$)$_2$), 2.7 (m, 1H, —CH—S), 3.2 (m, 2H, CH$_2$—CH$_2$—SO$_3$), 3.6-3.9 (m, 8H, SO$_3$CH$_2$, S—CH$_2$, CH$_3$O, CH—N), 4.9 (d, 1H, NH), 5.05 (s, 2H, O—CH$_2$—C$_6$H$_5$), 6.8 (m, 2H, S—C$_6$H$_4$), 7.2 (m, 2H, S—C$_6$H$_4$), 7.43 (m, 5H, H aromatic). ES$^+$: 588 M+Na$^+$.

Compound 4d 2,2-Dimethylpropyl 3-benzyloxycarbonylamino-4-(4-methoxybenzylsulfanyl)-5-phenylpentane-1-sulfonate Yield 76%. HPLC (80%): Tr=12.17 min. $^1$H NMR (CDCl$_3$): 0.9 (s, 9H, C(CH$_3$)$_3$), 1.6-1.8 (m, 2H, CH$_2$CH$_2$—SO$_3$), 2.6-3.1 (m, 5H, CH$_2$—CH—S, CH$_2$CH$_2$—SO$_3$), 3.4-3.6 (m, 2H, S—CH$_2$), 3.7-3.9 (m, 6H, SO$_3$CH$_2$, CH—N, CH$_3$O), 4.9 (d, 1H, NH), 5.15 (s, 2H, O—CH$_2$—C$_6$H$_5$), 6.75 (m, 2H, S—C$_6$H$_4$), 7.1 (m, 3H, H aromatic), 7.2 (m, 2H, H aromatic), 7.3-7.4 (m, 7H, H aromatic). ES$^+$: 622 M+Na$^+$.

Compound 4e 2,2-Dimethylpropyl 3-benzyloxycarbonylamino-4-(4-methoxybenzylsulfanyl)-6-phenylhexane-1-sulfonate Yield 74%. HPLC (90%): Tr=15.6 and 16.5 min. $^1$H NMR (CDCl$_3$): 0.9 (s, 9H, C(CH$_3$)$_3$), 1.8-2.1 (m, 4H, CH$_2$—CH—S, CH$_2$—CH$_2$—SO$_3$), 2.5 (m, 2H, CH$_2$—CH$_2$), 2.7-3.1 (m, 3H, CH—S, CH$_2$CH$_2$—SO$_3$), 3.6-3.8 (m, 7H, SO$_3$CH$_2$, S—CH$_2$, CH$_3$O), 3.95 (m, 1H, CH—N), 4.85 and 4.95 (d, 1H, NH), 5.15 (s, 2H, O—CH$_2$—C$_6$H$_5$), 6.8 (m, 2H, S—C$_6$H$_4$), 7.0-7.2 (m, 5H, H aromatic), 7.2 (m, 2H, S—C$_6$H$_4$), 7.43 (m, 5H, H aromatic). ES$^+$: 636 M+Na$^+$.

Compound 4f 2,2-Dimethylpropyl 3-benzyloxycarbonylamino-4-(4-methoxybenzylsulfanyl)-6-(4-methoxyphenyl)hexane-1-sulfonate Yield 59%. HPLC (80%): Tr=12.6 and 13.4 min. $^1$H NMR (CDCl$_3$): 0.9 (s, 9H, C(CH$_3$)$_3$), 1.8-2.1 (m, 4H, CH$_2$—CH—S, CH$_2$—CH$_2$—SO$_3$), 2.5 (m, 2H, CH$_2$—CH$_2$), 2.7-3.1 (m, 3H, CH—S, CH$_2$CH$_2$—SO$_3$), 3.6-3.8 (m, 10H, SO$_3$CH$_2$, S—CH$_2$, CH$_3$O, CH$_3$O), 3.95 (m, 1H, CH—N), 4.85 and 4.95 (d, 1H, NH), 5.15 (s, 2H, O—CH$_2$—C$_6$H$_5$), 6.8 (m, 4H, H aromatic), 6.9-7.1 (m, 4H, H aromatic), 7.43 (m, 5H, H aromatic). ES$^+$: 666 M+Na$^+$.

Compound 4g 2,2-Dimethylpropyl 3-benzyloxycarbonylamino-4-(4-methoxybenzylsulfanyl)-6-(2-methoxyphenyl)hexane-1-sulfonate Yield 83%. HPLC (80%): Tr=14.7 and 15.3 min, $^1$H NMR (CDCl$_3$): 0.9 (s, 9H, C(CH$_3$)$_3$), 1.7-2.1 (m, 4H, CH$_2$—CH—S, CH$_2$—CH$_2$—SO$_3$), 2.4 (m, 2H, CH$_2$—CH$_2$), 2.7-3.1 (m, 3H, CH—S, CH$_2$CH$_2$—SO$_3$), 3.6-3.8 (m, 10H, SO$_3$CH$_2$, S—CH$_2$, CH$_3$O, CH$_3$O), 4.0 (m, 1H, CH—N), 4.85 and 4.95 (d, 1H, NH), 5.15 (m, 2H, O—CH$_2$—C$_6$H$_5$), 6.8 (m, 4H, H aromatic), 6.9-7.1 (m, 4H, H aromatic), 7.43 (m, 5H, H aromatic). ES$^+$: 666 M+Na$^+$.

Compound 4h 2,2-Dimethylpropyl 3-benzyloxycarbonylamino-4-(4-methoxybenzylsulfanyl)-6-(4-bromophenyl)hexane-1-sulfonate Yield 91%. HPLC (80%): Tr=21.7 and 22.8 min. $^1$H NMR (CDCl$_3$): 0.9 (s, 9H, C(CH$_3$)$_3$), 1.6-1.9 (m, 4H, CH$_2$—CH—S, CH$_2$—CH$_2$—SO$_3$), 2.45 (m, 2H, CH$_2$—CH$_2$), 2.65 (m, 1H, CH—S), 3.1 (m, 2H, CH$_2$CH$_2$—SO$_3$), 3.5-3.8 (m, 7H, SO$_3$CH$_2$, S—CH$_2$, CH$_3$O), 3.95 (m, 1H, CH—N), 4.85 and 4.95 (d, 1H, NH), 5.1 (2H, S, O—CH$_2$—C$_6$H$_5$), 6.8 (m, 4H, H aromatic), 6.9-7.1 (m, 4H, H aromatic), 7.43 (m, 5H, H aromatic). ES$^+$: 700-702 M+Na$^+$.

Preparation 5: Synthesis of the Compounds 5

Anisole (5 equivalents) and trifluoroacetic acid (7 ml/mmol) are added to compound 4 (1 equivalent). The reaction mixture is brought to reflux under argon for 16 h. The solvent is eliminated under reduced pressure. The residue is suspended in 5 ml/mmol of cyclohexane, which is subsequently eliminated under reduced pressure. This operation is repeated twice in order to eliminate the traces of trifluoroacetic acid. Ether is added to the oil obtained, and the inhibitor 5 precipitates and is dried under reduced pressure after filtration.

The compounds 5a, 5b, 5c, 5d, 5e, 5f, 5g and 5h were obtained in the same manner and were characterized by means of their $^1$H NMR spectrum in CDCl$_3$ at 400 MHz and by electrospray mass spectroscopy.

Compound 5a

3-Amino-4-mercaptopentane-1-sulfonic acid

Yield 75%. $^1$H NMR (DMSO-D$_6$): 1.2 (d, 3H, J=7 Hz, CH$_3$), 1.8-2.0 (m, 2H, CH$_2$CH$_2$—SO$_3$), 2.6 (m, 2H, CH$_2$—CH$_2$—SO$_3$), 2.8 (m, 1H, —CH—S), 3.1 (m, 1H, CHN), 7.9 (s, 3H, NH$_3$$^+$). ES$^+$: 222 M+Na$^+$. ES$^-$: 198 M–H.

Compound 5b

3-Amino-4-mercapto-4-phenylbutane-1-sulfonic acid

Yield 69%. $^1$H NMR (DMSO-D$_6$): 1.8-2.1 (m, 2H, CH$_2$CH$_2$—SO$_3$), 2.5-2.7 (m, 3H, CH$_2$—CH$_2$—SO$_3$; CHS), 3.6 (m, 1H, CHN), 7.1 (m, 5H, H aromatic), 7.9 (s, 3H, NH$_3$$^+$). ES$^+$: 284 M+Na$^+$, ES$^-$: 260 M–H Compound 5c 3-Amino-4-mercapto-6-methylheptane-1-sulfonic acid Yield 50%. $^1$H NMR (DMSO-D$_6$): 0.7 and 0.8 (d, 6H, J=7 Hz, CH(CH$_3$)$_2$), 1.35 (m, 2H, CH$_2$—CH(CH$_3$)$_2$), 1.7-1.9 (m, 2H, CH$_2$CH$_2$—SO$_3$), 2.0 (m, 1H, CH(CH$_3$)$_2$), 2.7 (m, 2H, CH$_2$CH$_2$—SO$_3$), 3.0 (m, 1H, CHS), 3.3 (m, 1H, CH—N), 7.9 (s, 3H, NH$_3$$^+$). ES$^-$: 240 M–H.

Compound 5d

3-Amino-4-mercapto-5-phenylpentane-1-sulfonic acid

Yield 82%. $^1$H NMR (DMSO-D$_6$): 1.9-2.1 (m, 2H, CH$_2$CH$_2$—SO$_3$), 2.6-2.7 (m, 4H, CH$_2$—CH—S, CH$_2$CH$_2$—

SO$_3$), 2.9-3.1 (m, 1H, CHS), 3.4 (m, 1H, CH—N), 7.1 (m, 5H, H aromatic), 7.9 (s, 3H, NH$_3^+$). ES$^+$: 298 M+Na$^+$. ES$^-$: 274 M–H.

Compound 5e

3-Amino-4-mercapto-6-phenylhexane-1-sulfonic acid

Yield 55%. $^1$H NMR (DMSO-D$_6$): 1.6 (m, 1H, CH$_2$—CH—S), 1.7-2.0 (m, 3H, CH$_2$—CH$_2$—CH—S, CH$_2$CH$_2$—SO$_3$), 2.6-2.7 (m, 3H, CH$_2$—CH—S, CH$_2$CH$_2$—SO$_3$), 2.8 (m, 1H, CH$_2$—CH—S), 2.9 (m, 1H, CHS), 3.4 (m, 1H, CH—N), 7.1 (m, 5H, H aromatic), 7.9 (s, 3H, NH$_3^+$), ES$^-$: 288 M–H.

Compound 5f

3-Amino-4-mercapto-6-(4-methoxyphenyl)hexane-1-sulfonic acid

Yield 51%. $^1$H NMR (DMSO-D$_6$): 1.6 (m, 1H, CH$_2$—CH—S), 1.7-2.0 (m, 3H, CH$_2$—CH$_2$—CH—S, CH$_2$CH$_2$—SO$_3$), 2.6-2.8 (m, 4H, CH$_2$—CH—S, CH$_2$CH$_2$—SO$_3$), 2.9 (m, 1H, CHS), 3.4 (m, 1H, CH—N), 3.5-3.8 (m, 3H, OCH$_3$), 6.7 (m, 2H, H aromatic), 7.0 (m, 2H, H aromatic), 7.9 (s, 3H, NH$_3^+$). ES$^+$: 342 M+Na$^+$.

Compound 5g

3-Amino-4-mercapto-6-(2-methoxyphenyl)hexane-1-sulfonic acid

Yield 80%. $^1$H NMR (DMSO-D$_6$): 1.3-1.6 (m, 2H, CH$_2$—CHS), 1.7-2.1 (m, 2H, CH$_2$CH$_2$—SO$_3$), 2.5-2.8 (m, 4H, CH$_2$—CH—S, CH$_2$CH$_2$—SO$_3$), 2.9 (m, 1H, CHS), 3.4 (m, 1H, CH—N), 3.5-3.8 (m, 3H, OCH$_3$), 6.6-7.3 (m, 4H, H aromatic), 7.8 (s, 3H, NH$_3^+$). ES$^+$: 342 M+Na$^+$.

Compound 5h

3-Amino-4-mercapto-6-(4-bromophenyl)hexane-1-sulfonic acid

Yield 85%. $^1$H NMR (DMSO-D$_6$): 1.6 (m, 1H, CH$_2$—CH—S), 1.8-2.0 (m, 3H, CH$_2$—CH$_2$—CHS, CH$_2$CH$_2$—SO$_3$), 2.6 (m, 3H, CH$_2$—CH—S, CH$_2$CH$_2$—SO$_3$), 2.8 (m, 1H, CH$_2$—CH—S), 2.9 (m, 1H, CHS), 3.4-3.5 (m, 1H, CH—N), 7.1 (m, 2H, H aromatic), 7.4 (m, 2H, H aromatic), 7.9 (s, 3H, NH$_3^+$). ES$^+$: 390-392 M+Na$^+$.

Preparation 6: Synthesis of Compound 6

Ethyl (2E)-5-phenylpent-2-enoate 24.7 ml (164 mmol, 1.1 equivalents) of diazabicycloundecene (DBU) are added, under argon at 0° C., dropwise, to 32.6 ml (164 mmol, 1.1 equivalents) of triethyl phosphonoacetate in 150 ml of anhydrous dichloromethane. The mixture is stirred for 30 min. After a return to 25° C., 19.6 ml (149 mmol, 1 equivalent) of hydrocynamaldehyde are added. After reaction for 16 h, 150 ml of 1N HCl are added to the reaction medium. The organic phase is separated, and washed with 2×50 ml 1N HCl, then 2×50 ml 10% NaHCO$_3$. The organic phase is dried over Na$_2$SO$_4$ and concentrated under reduced pressure. The product is purified by filtration over silica. A colorless oil is obtained.

Yield 67%. $^1$H NMR (CDCl$_3$): 1.3 (t, 3H, J=7 Hz, CH$_3$—CH$_2$), 2.5 (q, 2H, J=7 Hz, Ph-CH$_2$—CH$_2$), 2.8 (t, 2H, J=7 Hz, Ph-CH$_2$—CH$_2$), 4.2 (q, 2H, J=7 Hz, CH$_3$—CH$_2$), 5.85 (d, 1H, J=12 Hz, CH=CH—CO), 7.0 (td, 1H, J=7 Hz, J=12 Hz, CH=CH—CO), 7.2 (m, 3H, H aromatic), 7.3 (m, 2H, H aromatic).

Preparation 7: Synthesis of Compounds 7a-b 7.3 g (35.7 mmol, 1 equivalent) of ethyl (2Z)-5-phenyl-pent-2-enoate are added, at 25° C., to a solution of 50 g (1.4 g/mmol) of AD-mix and of 0.36 g (3.7 mmol, 0.01 g/mmol) in a mixture of 160 ml (4.5 ml/mmol) of tert-butyl alcohol and of 160 ml (4.5 ml/mmol) of water. After reaction for 5 h, 45 g (357 mmol, 1.3 g/mmol, 10 equivalents) of sodium sulfite are added and the mixture is stirred for 30 min. After dilution of the reaction medium with 150 ml of ethyl acetate, the organic phase is separated, dried over Na$_2$SO$_4$ and then concentrated under reduced pressure. The product is purified by filtration over silica. A colorless oil is obtained.

Compounds 7a and 7b were characterized by thin layer chromatography (TLC) on a silica support with an eluent of cyclohexane: ethyl acetate, by means of their $^1$H NMR spectrum in CDCl$_3$ at 400 MHz and by means of their specific optical rotation.

Compound 7a

Ethyl (2R,3S)-2,3-dihydroxy-5-phenylpentanoate

Yield 70%. TLC (cyclohexane:ethyl acetate, 60:40): R$_f$=0.28 [α]20D=−29.8° (c=1, MeOH). HPLC (50% B): Rt=5.5 min. $^1$H NMR (CDCl$_3$): 1.3 (t, 3H, COOCH$_2$CH$_3$), 1.95 (m, 3H, OH, CH$_2$C—OH), 2.74 (m, 1H, CH$_2$Phe), 2.85 (m, 1H, CH$_2$Phe), 3.08 (d, 1H, OH), 3.93 (m, 1H, CHCH$_2$), 4.2 (d, 1H, CHCOOEt), 4.3 (q, 2H, COOCH$_2$CH$_3$), 7.15-7.35 (m, 5H, Ph).

Compound 7b

Ethyl (2S,3R)-2,3-dihydroxy-5-phenylpentanoate

Yield 72%. TLC (cyclohexane:ethyl acetate, 70:30): R$_f$=0.17. [α]$^{20}_D$=+28.7° (c=1.1, MeOH). HPLC (70% B): Rt=3.6 min. $^1$H NMR (CDCl$_3$): 1.3 (t, 3H, COOCH$_2$CH$_3$), 1.95 (m, 2H, CH$_2$C—OH), 2.75 (m, 1H, CH$_2$Phe), 2.85 (m, 1H, CH$_2$Phe), 3.93 (m, 1H, CHCH$_2$), 4.1 (d, 1H, CHCOOEt), 4.3 (q, 2H, COOCH$_2$CH$_3$), 7.15-7.35 (m, 5H, Ph).

Preparation 8: Synthesis of the Cyclic Sulfates 8a-b 2.1 ml (29 mmol, 1 equivalent) of thionyl chloride are added, at 0° C., dropwise, in 10 min, to a solution of 6.9 g (29 mmol, 1 equivalent) of compound 7 and of 8 ml (58 mmol, 2 equivalents) of triethylamine in 60 ml (2 ml/mmol) of anhydrous dichloromethane. The mixture is stirred for 5 min, diluted with 40 ml of ether and washed with 30 ml of water. The solvent is eliminated under reduced pressure and the residue is suspended in a mixture of 180 ml of water, 80 ml of chloroform and 80 ml of carbon tetrachloride, and then 9.6 g (45 mmol, 1.5 equivalents) of sodium periodate and a catalytic amount of RuCl$_3$ are added thereto. After stirring at 25° C. for 1 h, the mixture is diluted with 150 ml of ether and filtered over Cellite®. The organic phase is washed with 40 ml of 10% NaHCO$_3$, dried over Na$_2$SO$_4$ and then concentrated under reduced pressure. The product is purified by filtration over silica. A colorless oil is obtained.

Compounds 8a and 8b were characterized by TLC on a silica support with an eluant of cyclohexane: ethyl acetate, by means of their $^1$H NMR spectrum in CDCl$_3$ at 400 MHz and by means of their specific optical rotation.

Compound 8a

Yield: 78%. TLC (cyclohexane:ethyl acetate, 60:40): $R_f$=0.4. $[\alpha]^{20}_D$=−75.66° (c=1, MeOH). HPLC (70% B): Rt=7.2 min. $^1$H NMR (CDCl$_3$): 1.3 (t, 3H, COOCH$_2$CH$_3$), 2.3 (m, 2H, CH$_2$C—OH), 2.76 (m, 1H, CH$_2$Phe), 2.89 (m, 1H, CH$_2$Phe), 4.3 (q, 2H, COOCH$_2$CH$_3$), 4.87 (d, 1H, CHCOOEt), 4.9 (m, 1H, CHCH$_2$), 7.2-7.4 (m, 5H, Ph).

Compound 8b

Yield: 70%. TLC (cyclohexane:ethyl acetate 60:40): $R_f$=0.4. $[\alpha]^{20}_D$=+78.3° (c=1.1, MeOH). HPLC (70% B): Rt=7.24 min. $^1$H NMR (CDCl$_3$): 1.3 (t, 3H, COOCH$_2$CH$_3$), 2.3 (m, 2H, CH$_2$C—OH), 2.8 (m, 1H, CH$_2$Phe), 2.95 (m, 1H, CH$_2$Phe), 4.3 (q, 2H, COOCH$_2$CH$_3$), 4.87 (d, 1H, CHCOOEt), 4.9 (m, 1H, CHCH$_2$), 7.15-7.4 (m, 5H, Ph).

Preparation 9: Synthesis of compounds 9a-b 3.8 g (44 mmol, 4 equivalents) of lithium bromide are added to a solution of 3.3 g (11 mmol, 1 equivalent) of compound 8 in 110 ml (10 ml/mmol) of anhydrous THF. The mixture is stirred at 25° C. until compound 8 has completely disappeared. After concentration under reduced pressure, the residue is taken up with 150 ml of ether and 20 ml of water, and then 0.1 ml of 20% H$_2$SO$_4$ is added thereto. The solution is stirred at 4° C. for 24 h. The organic phase is separated, washed with 3×20 ml of 10% NaHCO$_3$, dried over Na$_2$SO$_4$, and then concentrated under reduced pressure. The product is purified by filtration over silica. A colorless oil is obtained.

Compounds 9a and 9b were characterized by TLC on a silica support with an eluant of cyclohexane: ethyl acetate, by means of their $^1$H NMR spectrum in CDCl$_3$ at 400 MHz and by means of their specific optical rotation.

Compound 9a

Ethyl (2S,3S)-2-bromo-3-hydroxy-5-phenylpentanoate

Yield: 85%. TLC (cyclohexane:ethyl acetate, 60:40): $R_f$=0.5. $[\alpha]^{20}_D$=−37.35° (c=1.004, MeOH). HPLC (70% B): Rt=6.6 min. $^1$H NMR (CDCl$_3$): 1.3 (t, 3H, COOCH$_2$CH$_3$), 1.83 (m, 1H, CH$_2$C—OH), 2.17 (m, 1H, CH$_2$C—OH), 2.75 (m, 2H, OH, CH$_2$Phe), 2.9 (m, 1H, CH$_2$Phe), 4.03 (m, 1H, CHCH$_2$), 4.15 (d, 1H, CHCOOEt), 4.27 (q, 2H, COOCH$_2$CH$_3$), 7.2-7.35 (m, 5H, Ph).

Compound 9b

Ethyl (2R,3R)-2-bromo-3-hydroxy-5-phenylpentanoate

Yield 91%. TLC (cyclohexane:ethyl acetate, 60:40): $R_f$=0.5. $[\alpha]^{20}_D$=+35.8° (c=1.85, MeOH). HPLC (70% B): Rt=6.6 min. $^1$H NMR (CDCl$_3$): 1.3 (t, 3H, COOCH$_2$CH$_3$), 1.83 (m, 1H, CH$_2$C—OH), 2.17 (m, 1H, CH$_2$C—OH), 2.75 (m, 2H, OH, CH$_2$Phe), 2.9 (m, 1H, CH$_2$Phe), 4.03 (m, 1H, CHCH$_2$), 4.15 (d, 1H, CHCOOEt), 4.27 (q, 2H, COOCH$_2$CH$_3$), 7.2-7.35 (m, 5H, Ph).

Preparation 10: Synthesis of Compounds 10a-d 1) 0.32 g (5 mmol, 1.25 equivalents) of sodium azide is added to a solution of 1.2 g (4 mmol, 1 equivalent) of compound 8 in 24 ml (6 ml/mmol) of acetone and 2.5 ml (0.6 ml/mmol) of water. The mixture is stirred at 25° C. until compound 8 has completely disappeared. After concentration under reduced pressure, the residue is taken up with 50 ml of ether and 5 ml of water, and then 1 ml of 20% H$_2$SO$_4$ is added thereto. The solution is stirred at 4° C. for 24 h. The organic phase is separated, washed with 3×20 ml of 10% NaHCO$_3$, dried over Na$_2$SO$_4$, and then concentrated under reduced pressure. The product is purified by filtration over silica. A colorless oil is obtained.

Compounds 10a, 10b, 10c and 10d were characterized by TLC on a silica support with an eluant of cyclohexane: ethyl acetate, by means of their $^1$H NMR spectrum in CDCl$_3$ at 400 MHz and by means of their specific optical rotation.

Compound 10a

Ethyl (2S,3S)-2-azido-3-hydroxy-5-phenylpentanoate

Yield: 84%. TLC (cyclohexane:ethyl acetate, 60:40): $R_f$=0.55. $[\alpha]^{20}_D$=−28.7° (c=1, MeOH). HPLC (70% B): Rt=5.65 min. $^1$H NMR (CDCl$_3$): 1.3 (3H, t, COOCH$_2$CH$_3$), 1.9 (2H, m, CH$_2$C—OH), 2.37 (1H, d, OH), 2.7 (1H, m, CH$_2$Phe), 2.9 (1H, m, CH$_2$Phe), 3.95 (1H, m, CHCH$_2$), 3.97 (1H, d, CHCOOEt), 4.3 (2H, q, COOCH$_2$CH$_3$), 7.2-7.35 (5H, m, Ph).

Compound 10c

Ethyl (2R,3S)-2-azido-3-hydroxy-5-phenylpentanoate

Yield: 86%. TLC (cyclohexane:ethyl acetate, 60:40): $R_f$=0.58. $[\alpha]^{20}_D$=+15° (c=1.082, MeOH). HPLC (70% B): Rt=5.72 min. $^1$H NMR (CDCl$_3$): 1.35 (t, 3H, COOCH$_2$CH$_3$), 1.86 (m, 1H, CH$_2$C—OH), 1.96 (m, 1H, CH$_2$C—OH), 2.15 (d, 1H, OH), 2.70 (m, 1H, CH$_2$Phe), 2.85 (m, 1H, CH$_2$Phe), 3.9 (d, 1H, CHCOOEt), 4.07 (m, 1H, CHCH$_2$), 4.3 (q, 2H, COOCH$_2$CH$_3$), 7.15-7.35 (m, 5H, Ph).

2) 1.12 g (17.2 mmol, 2 equivalents) of sodium azide are added to 2.6 g (8.6 mmol, 1 equivalent) of compound 9 in 9 ml (1 ml/mmol) of anhydrous dimethyl sulfoxide. The reaction medium is stirred at 25° C. overnight, and then diluted with 90 ml of a 2:1 mixture of cyclohexane and dichloromethane. The organic phase is washed with 3×10 ml of H$_2$O and 1×10 ml of a saturated NaCl solution and dried over Na$_2$SO$_4$, then concentrated under reduced pressure. The product is purified by filtration over silica. A colorless oil is obtained.

Compound 10b

Ethyl (2R,3R)-2-azido-3-hydroxy-5-phenylpentanoate

Yield: 84%. TLC (cyclohexane:ethyl acetate, 70:30): $R_f$=0.38. $[\alpha]^{20}_D$=+28.5° (c=1, MeOH). HPLC (70% B): Rt=5.63 min. 1H NMR (CDCl$_3$): 1.3 (3H, t, COOCH$_2$CH$_3$), 1.9 (2H, m, CH$_2$C—OH), 2.37 (1H, d, OH), 2.7 (1H, m, CH$_2$Phe), 2.9 (1H, m, CH$_2$Phe), 3.95 (1H, m, CHCH$_2$), 3.97 (1H, d, CHCOOEt), 4.3 (2H, q, COOCH$_2$CH$_3$), 7.2-7.35 (5H, m, Ph).

Compound 10d

Ethyl (2S,3R)-2-azido-3-hydroxy-5-phenylpentanoate

Yield: 69%. TLC (cyclohexane:ethyl acetate, 60:40): $R_f$=0.58. $[\alpha]^{20}_D$=−11.7° (c=0.95, MeOH). HPLC (70% B): Rt=5.76 min. $^1$H NMR (CDCl$_3$): 1.35 (t, 3H, COOCH$_2$CH$_3$), 1.86 (m, 1H, CH$_2$C—OH), 1.96 (m, 1H, CH$_2$C—OH), 2.15 (d, 1H, OH), 2.70 (m, 1H, CH$_2$Phe), 2.85 (m, 1H, CH$_2$Phe), 3.9 (d, 1H, CHCOOEt), 4.07 (m, 1H, CHCH$_2$), 4.3 (q, 2H, COOCH$_2$CH$_3$), 7.15-7.35 (m, 5H, Ph).

Preparation 11: Synthesis of compounds 11a-d 1.49 g (5.7 mmol, 1 equivalent) of triphenylphosphine are added to 1.5 g (5.7 mmol, 1 equivalent) of compound 10, in 23 ml (4 ml/mmol) of acetonitrile. The mixture is stirred at 25° C. for one hour, and is then brought to reflux for five hours. After concentration of the reaction medium under reduced pressure, the oil is purified by filtration over silica. A colorless oil is obtained.

Compounds 11a, 11b, 11c and 11d were characterized by TLC on a silica support with an eluant of cyclohexane: ethyl acetate, by means of their $^1$H NMR spectrum in CDCl$_3$ at 400 MHz and by means of their specific optical rotation.

Compound 11a

Ethyl (2S,3R)-3-phenethylaziridine-2-carboxylate

Yield: 84%. TLC (cyclohexane:ethyl acetate, 60:40): $R_f$=0.26. $[\alpha]^{20}_D$=+70° (c=1.024, MeOH). HPLC (40% B): Rt=4.84 min. $^1$H NMR (CDCl$_3$): 1.3 (t, 3H, COOCH$_2$CH$_3$), 1.8 (m, 2H, CH$_2$C—NH), 2.3 (m, 1H, CHCH$_2$), 2.33 (s, 1H, CHCOOEt), 2.8 (m, 2H, CH$_2$Phe), 4.2 (q, 2H, COOCH$_2$CH$_3$), 7.2-7.35 (m, 5H, Ph).

Compound 11b

Ethyl (2R,3R)-3-phenethylaziridine-2-carboxylate

Yield: 68%. TLC (cyclohexane:ethyl acetate, 50:50): $R_f$=0.31. $[\alpha]^{20}_D$=−14.38° (c=1.05, MeOH). HPLC (40% B): Rt=4.15 min. $^1$H NMR (CDCl$_3$): 1.3 (t, 3H, COOCH$_2$CH$_3$), 1.85 (m, 1H, CH$_2$C—NH), 1.97 (m, 1H, CH$_2$C—NH), 2.27 (m, 1H, CHCH$_2$), 2.63 (d, 1H, CHCOOEt), 2.68-2.85 (m, 2H, CH$_2$Phe), 4.18 (2q, 2H, COOCH$_2$CH$_3$), 7.1-7.25 (m, 3H, Ph), 7.25-7.35 (m, 2H, Ph).

Compound 11c

Ethyl (2R,3S)-3-phenethylaziridine-2-carboxylate

Yield: 72%. TLC (cyclohexane:ethyl acetate, 70:30): $R_f$=0.2. $[\alpha]^{20}_D$=−67.38° (c=1, MeOH). HPLC (70% B): Rt=2.73 min. $^1$H NMR (CDCl$_3$): 1.3 (t, 3H, COOCH$_2$CH$_3$), 1.8 (m, 2H, CH$_2$C—NH), 2.3 (m, 1H, CHCH$_2$), 2.33 (s, 1H, CHCOOEt), 2.8 (m, 2H, CH$_2$Phe), 4.2 (q, 2H, COOCH$_2$CH$_3$), 7.2-7.35 (m, 5H, Ph).

Compound 11d

Ethyl (2S,3S)-3-phenethylaziridine-2-carboxylate

Yield: 50%. TLC (cyclohexane:ethyl acetate, 50:50): $R_f$=0.31. $[\alpha]^{20}_D$=+12.83 (c=1, MeOH). HPLC (40% B): Rt=4.07 min. $^1$H NMR (CDCl$_3$): 1.3 (t, 3H, COOCH$_2$CH$_3$), 1.85 (m, 1H, CH$_2$C—NH), 1.97 (m, 1H, CH$_2$C—NH), 2.27 (m, 1H, CHCH$_2$), 2.63 (d, 1H, CHCOOEt), 2.68-2.85 (m, 2H, CH$_2$Phe), 4.18 (2q, 2H, COOCH$_2$CH$_3$), 7.1-7.25 (m, 3H, Ph), 7.25-7.35 (m, 2H, Ph).

Preparation 12: Synthesis of Compounds 12a-d 1.14 g (4.6 mmol, 2 equivalents) of benzyloxycarbonylsuccinimide and 0.03 g (0.24 mmol, 0.1 equivalent) of 4-dimethylaminopyridine are added to 0.5 g (2.3 mmol, 1 equivalent) of compound 11, in 9 ml (4 ml/mmol) of pyridine. The mixture is stirred at 4° C. for 24 h. After concentration of the reaction medium under reduced pressure, the oil is purified by filtration over silica. A colorless oil is obtained.

Compounds 12a, 12b, 12c and 12d were characterized by TLC on a silica support with an eluant of cyclohexane: ethyl acetate, by means of their $^1$H NMR spectrum in CDCl$_3$ at 400 MHz and by means of their specific optical rotation.

Compound 12a

Ethyl (2S,3R)-N-benzyloxycarbonyl-3-phenethylaziridine-2-carboxylate

Yield: 93%. TLC (cyclohexane:ethyl acetate, 70:30): $R_f$=0.47. $[\alpha]^{20}_D$=+30.2° (c=1.026, MeOH). HPLC (70% B): Rt=13.7 min. $^1$H NMR (CDCl$_3$): 1.25 (t, 3H, COOCH$_2$CH$_3$), 1.87 (m, 2H, CH$_2$C—NH), 2.7-2.9 (m, 4H, CH$_2$Phe, CHCH$_2$, CHCOOEt), 4.15 (q, 2H, COOCH$_2$CH$_3$), 5.15 (2d, 2H, OCH$_2$Phe), 7.15-7.3 (m, 5H, Ph), 7.3-7.4 (m, 5H, Ph).

Compound 12b

Ethyl (2R,3R)-N-benzyloxycarbonyl-3-phenethylaziridine-2-carboxylate

Yield: 91%. TLC (cyclohexane:ethyl acetate, 80:20): $R_f$=0.27. $[\alpha]^{20}_D$=+42.49° (c=1.024, MeOH). HPLC (80% B): Rt=6.6 min. $^1$H NMR (CDCl$_3$): 1.3 (t, 3H, COOCH$_2$CH$_3$), 1.9-2 (m, 2H, CH$_2$C—NH), 2.75 (m, 2H, CH$_2$Phe, 2.85 (m, 1H, CHCH$_2$), 3.2 (d, 1H, CHCOOEt), 4.2 (q, 2H, COOCH$_2$CH$_3$), 5.15 (m, 2H, OCH$_2$Phe), 7.1-7.3 (m, 5H, Ph), 7.3-7.4 (m, 5H, Ph).

Compound 12c

Ethyl (2R,3S)-N-benzyloxycarbonyl-3-phenethylaziridine-2-carboxylate

Yield: 90%. TLC (cyclohexane:ethyl acetate, 70:30): $R_f$=0.47. $[\alpha]^{20}_D$=−28.6° (c=1.05, MeOH). HPLC (70% B): Rt=13.84 min. $^1$H NMR (CDCl$_3$): 1.25 (t, 3H, COOCH$_2$CH$_3$), 1.87 (m, 2H, CH$_2$C—NH), 2.7-2.9 (m, 4H, CH$_2$Phe, CHCH$_2$, CHCOOEt), 4.15 (q, 2H, COOCH$_2$CH$_3$), 5.15 (2d, 2H, OCH$_2$Phe), 7.15-7.3 (m, 5H, Ph), 7.3-7.4 (m, 5H, Ph).

Compound 12d

Ethyl (2S,3S)-N-benzyloxycarbonyl-3-phenethylaziridine-2-carboxylate

Yield: 81%. TLC (cyclohexane:ethyl acetate, 70:30): $R_f$=0.49. $[\alpha]^{20}_D$=−39.58° (c=0.53, MeOH). HPLC (70% B): Rt=11.43 min. $^1$H NMR (CDCl$_3$): 1.3 (t, 3H, COOCH$_2$CH$_3$), 1.9-2 (m, 2H, CH$_2$C—NH), 2.75 (m, 2H, CH$_2$Phe, 2.85 (m, 1H, CHCH$_2$), 3.2 (d, 1H, CHCOOEt), 4.2 (q, 2H, COOCH$_2$CH$_3$), 5.15 (m, 2H, OCH$_2$Phe), 7.1-7.3 (m, 5H, Ph), 7.3-7.4 (m, 5H, Ph).

Preparation 13: Synthesis of Compounds $2e_{1-4}$ 1.0 g, 1 ml (6.4 mmol, 3.6 equivalents) of 4-methoxybenzylmercaptan and then, dropwise, 0.7 ml (5.5 mmol, 3 equivalents) of BF$_3$ etherate are added successively to a solution, cooled to 0° C., of 0.65 g (1.8 mmol, 1 equivalent) of compound 12, in 11 ml (6 ml/mmol) of anhydrous dichloromethane. The mixture is stirred at 4° C. for 24 h. After addition of 18 ml of 10% NaHCO$_3$ (10 ml/mmol) and of 18 ml of dichloromethane, the organic phase is separated, dried over Na$_2$SO$_4$ and concentrated under reduced pressure. The oil obtained is purified by filtration over silica. A colorless oil is obtained.

Compounds $2e_{1-4}$ were characterized by TLC on a silica support with an eluant of cyclohexane: ethyl acetate, by means of their $^1$H NMR spectrum in CDCl$_3$ at 400 MHz and by means of their specific optical rotation.

Compound 2e$_1$

Ethyl (2S,3R)-2-benzyloxycarbonylamino-3-(4-methoxybenzylsulfanyl)-5-phenylpentanoate Yield: 38%. TLC (n-heptane: ethyl acetate, 75:25): R$_f$=0.25. $[\alpha]^{20}_D$=−96.1° (c=0.282, MeOH). HPLC (70% B): Rt=23 min. $^1$H NMR (CDCl$_3$): 1.15 (t, 3H, COOCH$_2$CH$_3$), 1.75 (m, 1H, CH$_2$CHS), 1.8 (m, 1H, CH$_2$CHS), 2.55 (m, 1H, CHS), 2.76 (m, 1H, CH$_2$Phe), 2.83 (m, 1H, CH$_2$Phe), 3.7 (2d, 2H, SCH$_2$), 3.8 (s, 3H, OCH$_3$), 3.96-4.17 (m, 2H, COOCH$_2$CH$_3$), 4.65 (dd, 1H, CHCOOEt), 5.13 (m, 2H, OCH$_2$Phe), 5.43 (d, 1H, NH), 6.83 (d, 2H, Ar), 6.96 (d, 2H, Ar), 7.1-7.25 (m, 5H, Ph) 7.3-7.4 (m, 5H, Ph).

Compound 2e$_2$

Ethyl (2S,3S)-2-benzyloxycarbonylamino-3-(4-methyl-benzylsulfanyl)-5-phenylpentanoate Yield: 79%. TLC (cyclohexane:ethyl acetate, 70:30): R$_f$=0.36. $[\alpha]^{20}_D$=−19° (c=1.004, MeOH). HPLC (80% B): Rt=11.8 min. $^1$H NMR (CDCl$_3$): 1.25 (t, 3H, COOCH$_2$CH$_3$), 1.77 (m, 1H, CH$_2$CHS), 1.93 (m, 1H, CH$_2$CHS), 2.6-2.77 (m, 2H, CH$_2$Phe), 3.1 (m, 1H, CHS), 3.57 (s, 2H, SCH$_2$), 3.8 (s, 3H, OCH$_3$), 4.07-4.23 (2m, 2H, COOCH$_2$CH$_3$), 4.7 (d, 1H, CHCOOEt), 5.13 (s, 2H, OCH$_2$Phe), 5.55 (d, 1H, NH), 6.8 (d, 2H, Ar), 7.1 (d, 2H, Ar), 7.15-7.4 (m, 10H, Ph).

Compound 2e$_3$

Ethyl (2R,3S)-2-benzyloxycarbonylamino-3-(4-methylbenzylsulfanyl)-5-phenylpentanoate Yield: 43%. TLC (cyclohexane:ethyl acetate 80:20): R$_f$=0.24. $[\alpha]^{20}_D$=+96.0° (c=0.3, MeOH). HPLC (70% B): Rt=23 min. $^1$H NMR (CDCl$_3$): 1.15 (t, 3H, COOCH$_2$CH$_3$), 1.75 (m, 1H, CH$_2$CHS), 1.8 (m, 1H, CH$_2$CHS), 2.55 (m, 1H, CHS), 2.76 (m, 1H, CH$_2$Phe), 2.83 (m, 1H, CH$_2$Phe), 3.7 (2d, 2H, SCH$_2$), 3.8 (s, 3H, OCH$_3$), 3.96-4.17 (m, 2H, COOCH$_2$CH$_3$), 4.65 (dd, 1H, CHCOOEt), 5.13 (m, 2H, OCH$_2$Phe), 5.43 (d, 1H, NH), 6.83 (d, 2H, Ar), 6.96 (d, 2H, Ar), 7.1-7.25 (m, 5H, Ph) 7.3-7.4 (m, 5H, Ph).

Compound 2e$_4$

Ethyl (2R,3R)-2-benzyloxycarbonylamino-3-(4-methylbenzylsulfanyl)-5-phenylpentanoate Yield: 64%. TLC (cyclohexane:ethyl acetate, 70:30): R$_f$=0.36. $[\alpha]^{20}_D$=+20.2° (c=0.5, MeOH). HPLC (70% B): Rt=25.81 min. $^1$H NMR (CDCl$_3$): 1.25 (t, 3H, COOCH$_2$CH$_3$), 1.77 (m, 1H, CH$_2$CHS), 1.93 (m, 1H, CH$_2$CHS), 2.6-2.77 (m, 2H, CH$_2$Phe), 3.1 (m, 1H, CHS), 3.57 (s, 2H, SCH$_2$), 3.8 (s, 3H, OCH$_3$), 4.07-4.23 (2m, 2H, COOCH$_2$CH$_3$), 4.7 (d, 1H, CHCOOEt), 5.13 (s, 2H, OCH$_2$Phe), 5.55 (d, 1H, NH), 6.8 (d, 2H, Ar), 7.1 (d, 2H, Ar), 7.15-7.4 (m, 10H, Ph).

Preparation 14: Syntheses of Compounds 3e$_{1-4}$

A 1.6M solution of n-butyllithium in hexane (2 equivalents) is added dropwise, at −78° C., to a solution of neopentyl diethoxyphosphorylmethanesulfonate (2.0 equivalents) in anhydrous THF (4.5 ml/mmol). After stirring for 30 min, a solution of compound 2 (1 equivalent) in anhydrous THF (1 ml/mmol) is added, followed by the introduction, dropwise, of a 1.6M solution of diisobutylaluminum hydride in toluene (2 equivalents). The reaction mixture is maintained at −78° C. for 4 h, and is subsequently left to return to ambient temperature overnight. The solvents are eliminated under reduced pressure, and 10 ml/mmol of ether and 5 ml/mmol of 2N HCl are added to the residue. The mixture is stirred for 30 min, the organic phase is separated, and the aqueous phase is extracted twice with an equivalent volume of ether. The organic phases are combined, dried over Na$_2$SO$_4$ and concentrated under reduced pressure. The oil obtained is purified by silica chromatography. After elimination of the solvents, product 3 is obtained in the form of an oil.

Compounds 3e$_{1-4}$ were characterized by TLC on a silica support with an eluant of cyclohexane: ethyl acetate, by means of their $^1$H NMR spectrum in CDCl$_3$ at 400 MHz and by means of their specific optical rotation.

Compound 3e$_1$ 2,2-Dimethylpropyl (3R,4S)-3-benzyloxycarbonylamino-4-(4-methoxybenzylsulfanyl)-6-phenylhex-1-ene-1-sulfonate Yield: 27%. TLC (cyclohexane:ethyl acetate, 80:20): R$_f$=0.17. $[\alpha]^{20}_D$=−39.2° (c=1.1, MeOH). HPLC (80% B): Rt=15.33 min. $^1$H NMR (CDCl$_3$): 0.95 (s, 9H, 3× CH$_3$), 1.8 (m, 1H, CH$_2$CHS), 1.93 (m, 1H, CH$_2$CHS), 2.65 (m, 2H, CH$_2$Phe), 2.83 (m, 1H, CHS), 3.6-3.7 (m, 2H, SO$_3$CH$_2$), 3.7 (s, 2H, SCH$_2$), 3.75 (s, 3H, OCH$_3$), 4.63 (m, 1H, CHNH), 5.07 (m, 3H, OCH$_2$Phe, NH), 6.3 (d, 1H, C=CHSO$_3$), 6.75 (dd, 1H, CH=CSO$_3$), 8.8 (d, 2H, Ar), 7.07 (d, 2H, Ar), 7.1-7.5 (m, 10H, Ph).

Compound 3e$_2$ 2,2-Dimethylpropyl (3S,4S)-3-benzyloxycarbonylamino-4-(4-methoxybenzylsulfanyl)-6-phenylhex-1-ene-1-sulfonate Yield: 54%. TLC (cyclohexane:ethyl acetate, 80:20): R$_f$=0.37. $[\alpha]^{20}_D$=56.5° (c=1.01, MeOH). HPLC (80% B): Rt=16.37 min. $^1$H NMR (CDCl$_3$): 0.95 (s, 9H, 3× CH$_3$), 1.7-1.9 (m, 2H, CH$_2$CHS), 2.5-2.8 (m, 3H, CH$_2$Phe, CHS), 3.63 (s, 2H, SO$_3$CH$_2$), 3.7-3.85 (2d, 2H, SCH$_2$, s, 3H, OCH$_3$), 4.75 (m, 1H, CHNH), 5.1 (m, 2H, OCH$_2$Phe), 5.2 (d, 1H, NH), 6.35 (d, 1H, C=CHSO$_3$), 6.75-6.9 (m, 3H, CH=CSO$_3$, Ar), 7 (d, 2H, Ar), 7.15-7.4 (m, 10H, Ph).

Compound 3e$_3$ 2,2-Dimethylpropyl (3S,4R)-3-benzyloxycarbonylamino-4-(4-methoxybenzylsulfanyl)-6-phenylhex-1-ene-1-sulfonate Yield: 20%. TLC (cyclohexane:ethyl acetate, 80:20): R$_f$=0.17 $[\alpha]^{20}_D$=+38.5° (c=1.0, MeOH). HPLC (80% B): Rt=15.33 min. $^1$H NMR (CDCl$_3$): 0.95 (s, 9H, 3× CH$_3$), 1.8 (m, 1H, CH$_2$CHS), 1.93 (m, 1H, CH$_2$CHS), 2.65 (m, 2H, CH$_2$Phe), 2.83 (m, 1H, CHS), 3.6-3.7 (m, 2H, SO$_3$CH$_2$), 3.7 (s, 2H, SCH$_2$), 3.75 (s, 3H, OCH$_3$), 4.63 (m, 1H, CHNH), 5.07 (m, 3H, OCH$_2$Phe, NH), 6.3 (d, 1H, C=CHSO$_3$), 6.75 (dd, 1H, CH=CSO$_3$), 6.8 (d, 2H, Ar), 7.07 (d, 2H, Ar), 7.1-7.5 (m, 10H, Ph).

Compound 3e₄

2,2-Dimethylpropyl (3R,4R)-3-benzyloxycarbonylamino-4-(4-methoxybenzylsulfanyl)-6-phenylhex-1-ene-1-sulfonate Yield: 35%. TLC (cyclohexane:ethyl acetate, 80:20): $R_f$=0.37. $[\alpha]^{20}_D$=+55.4° (c=0.95, MeOH). HPLC (80% B): Rt=16.37 min. ¹H NMR (CDCl₃): 0.95 (s, 9H, 3× CH₃), 1.7-1.9 (m, 2H, CH₂CHS), 2.5-2.8 (m, 3H, CH₂Phe, CHS), 3.63 (s, 2H, SO₃CH₂), 3.7-3.85 (2d, 2H, SCH₂, s, 3H, OCH₃), 4.75 (m, 1H, CHNH), 5.1 (m, 2H, OCH₂Phe), 5.2 (d, 1H, NH), 6.35 (d, 1H, C=CHSO₃), 6.75-6.9 (m, 3H, CH=CSO₃, Ar), 7 (d, 2H, Ar), 7.15-7.4 (m, 10H, Ph)

Preparation 15: Synthesis of Compounds 4e₁₋₄

Sodium borohydride (1 equivalent) is added to a solution of a compound 3 (1 equivalent) in absolute ethanol (5 ml/mmol). The reaction mixture is stirred at 25° C. overnight. The solvents are eliminated under reduced pressure, and 10 ml/mmol of ethyl acetate and 5 ml/mmol of water are added to the residue. The organic phase is separated, and the aqueous phase is extracted twice with an equivalent volume of ethyl acetate. The organic phases are combined, dried over Na₂SO₄ and concentrated under reduced pressure. The oil obtained is purified by semi-preparative HPLC. After elimination of the solvents, product 16 is obtained in the form of an oil.

Compounds 4e₁₋₄ were characterized by TLC on a silica support with an eluant of cyclohexane: ethyl acetate, by means of their ¹H NMR spectrum in CDCl₃ at 400 MHz and by means of their specific optical rotation.

Compound 4e₁

2,2-Dimethylpropyl (3R,4S)-3-benzyloxycarbonylamino-4-(4-methoxybenzylsulfanyl)-6-phenylhexane-1-sulfonate Yield: 60%. TLC (cyclohexane:ethyl acetate, 80:20): $R_f$=0.15. $[\alpha]^{20}_D$=−33.7° (c=0.4, MeOH). HPLC (80% B): Rt=14.37 min. ¹H NMR (CDCl₃): 0.97 (s, 9H, 3× CH₃), 1.8 (m, 1H, CH₂CHS), 1.9 (m, 1H, CH₂CHS)), 1.9-2.05 (m, 2H, CH₂C—NH), 2.6 (m, 2H, CH₂Phe), 2.8 (m, 1H, CHS), 3.07 (m, 2H, CH₂SO₃), 3.63 (m, 2H, SO₃CH₂), 3.75 (s, 3H, OCH₃), 3.83 (s, 2H, SCH₂), 3.93 (m, 1H, CHNH), 4.97 (d, 1H, NH), 5.05 (m, 2H, OCH₂Phe), 6.8 (d, 2H, Ar), 7.07 (d, 2H, Ar), 7.1-7.4 (m, 10H, Ph).

Compound 4e₂

2,2-Dimethylpropyl (3S,4S)-3-benzyloxycarbonylamino-4-(4-methoxybenzylsulfanyl)-6-phenylhexane-1-sulfonate Yield: 63%. TLC (cyclohexane:ethyl acetate, 80:20): $R_f$=0.12. $[\alpha]^{20}_D$=−36.4° (c=0.936, MeOH). HPLC (80% B): Rt=15.2 min. ¹H NMR (CDCl₃): 1 (s, 9H, 3× CH₃), 1.75 (m, 1H, CH₂CHS), 1.8-2.1 (m, 3H, CH₂CHS, CH₂C—NH), 2.5 (m, 1H, CHS), 2.6 (m, 1H, CH₂Phe), 2.73 (m, 1H, CH₂Phe), 3 (m, 2H, CH₂SO₃), 3.67 (m, 2H, SO₃CH₂), 3.8 (s, 3H, OCH₃), 3.83 (s, 2H, SCH₂), 3.97 (m, 1H, CHNH), 4.9 (d, 1H, NH), 5.1 (m, 2H, OCH₂Phe), 6.83 (d, 2H, Ar), 7.05 (d, 2H, Ar), 7.1-7.4 (m, 10H, Ph).

Compound 4e₃

2,2-Dimethylpropyl (3S,4R)-3-benzyloxycarbonylamino-4-(4-methoxybenzylsulfanyl)-6-phenylhexane-1-sulfonate Yield: 83%. TLC (cyclohexane:ethyl acetate, 80:20): $R_f$=0.15. $[\alpha]^{20}_D$=+31.7° (c=0.4, MeOH). HPLC (80% B): Rt=14.25 min. ¹H NMR (CDCl₃): 0.97 (s, 9H, 3× CH₃), 1.8 (m, 1H, CH₂CHS), 1.9 (m, 1H, CH₂CHS)), 1.9-2.05 (m, 2H, CH₂C—NH), 2.6 (m, 2H, CH₂Phe), 2.8 (m, 1H, CHS), 3.07 (m, 2H, CH₂SO₃), 3.63 (m, 2H, SO₃CH₂), 3.75 (s, 3H, OCH₃), 3.83 (s, 2H, SCH₂), 3.93 (m, 1H, CHNH), 4.97 (d, 1H, NH), 5.05 (m, 2H, OCH₂Phe), 6.8 (d, 2H, Ar), 7.07 (d, 2H, Ar), 7.1-7.4 (m, 10H, Ph).

Compound 4e₄

2,2-Dimethylpropyl (3S,4R)-3-benzyloxycarbonylamino-4-(4-methoxybenzylsulfanyl)-6-phenylhexane-1-sulfonate Yield: 67%. TLC (cyclohexane:ethyl acetate, 80:20): $R_f$=0.12. $[\alpha]^{20}_D$=+35.8° (c=0.8, MeOH). HPLC (80% B): Rt=15.0 min. ¹H NMR (CDCl₃): 1 (s, 9H, 3× CH₃), 1.75 (m, 1H, CH₂CHS), 1.8-2.1 (m, 3H, CH₂CHS, CH₂C—NH), 2.5 (m, 1H, CHS), 2.6 (m, 1H, CH₂Phe), 2.73 (m, 1H, CH₂Phe), 3 (m, 2H, CH₂SO₃), 3.67 (m, 2H, SO₃CH₂), 3.8 (s, 3H, OCH₃), 3.83 (s, 2H, SCH₂), 3.97 (m, 1H, CHNH), 4.9 (d, 1H, NH), 5.1 (m, 2H, OCH₂Phe), 6.83 (d, 2H, Ar), 7.05 (d, 2H, Ar), 7.1-7.4 (m, 10H, Ph).

Preparation 16: Synthesis of Compounds 5e₁₋₄

Anisole (5 equivalents) and trifluoroacetic acid (7 ml/mmol) are added to compound 4 (1 equivalent). The reaction mixture is brought to reflux under argon for 16 hours. The solvent is eliminated under reduced pressure. The residue is suspended in 5 ml/mmol of cyclohexane, which is subsequently eliminated under reduced pressure. This operation is repeated twice in order to eliminate the traces of trifluoroacetic acid (TFA). Ether is added to the oil obtained, and compound 5 precipitates and is dried under reduced pressure after filtration. Compound 5 is subsequently purified by semi-preparative HPLC. After lyophilization, a colorless solid is obtained.

Compounds 5e₁₋₄ were characterized by means of their ¹H NMR spectrum in DMSO-D₆+TFA at 400 MHz and by means of their specific optical rotation.

Compound 5e₁

(3R,4S)-3-Amino-4-mercapto-6-phenylhexane-1-sulfonic acid

Yield: 54%. $[\alpha]^{20}_D$=−19.8 (c=0.77, H₂O). HPLC (gradient 10-90% B in 30 min): Rt=12.66 min. ES-MS[M+Na]⁺ 312. ¹H NMR (DMSO-D₆+TFA): 1.65 (m, 1H, CH₂CHS), 1.73-2 (m, 3H, CH₂CHS, CH₂C—NH₂), 2.6 (m, 3H, CH₂SO₃H, CH₂Phe) 2.8 (m, 1H, CH₂Phe), 2.93 (m, 1H, CHSH), 3.47 (m, 1H, CHNH₂), 7.1-7.3 (m, 5H, Ph), 7.9 (s, 3H, NH₃⁺).

Compound 5e₂

(3S,4S)-3-Amino-4-mercapto-6-phenylhexane-1-sulfonic acid

Yield: 49%. $[\alpha]^{20}_D$=−33.9 (c=0.44, H₂O), HPLC (gradient 10-90% B in 30 min): Rt=12.68 min. ES-MS[M+Na]⁺ 312. ¹H NMR (DMSO-D₆+TFA): 1.65 (m, 1H, CH₂CHS), 1.87

(m, 1H, CH$_2$CHS), 1.97 (m, 2H, CH$_2$C—NH$_2$), 2.6 (m, 3H, CH$_2$SO$_3$H, CH$_2$Phe), 2.8 (m, 1H, CH$_2$Phe), 2.93 (m, 1H, CHSH), 3.4 (m, 1H, CHNH$_2$), 7-7.3 (m, 5H, Ph), 7.9 (s, 3H, NH$_3^+$).

Compound 5e$_3$ (3S,4R)-3-Amino-4-mercapto-6-phenylhexane-1-sulfonic acid

Yield: 40%. [α]$^{20}_D$=+22.4 (c=0.1, H$_2$O)° HPLC (gradient 10-90% B in 30 min): Rt=12.63 min. ES-MS[M+Na]$^+$ 312.17. $^1$H NMR (DMSO-D$_6$+TFA): 1.65 (m, 1H, CH$_2$CHS), 1.73-2 (m, 3H, CH$_2$CHS, CH$_2$C—NH$_2$), 2.6 (m, 3H, CH$_2$SO$_3$H, CH$_2$Phe), 2.8 (m, 1H, CH$_2$Phe), 2.93 (m, 1H, CHSH), 3.47 (m, 1H, CHNH$_2$), 7.1-7.3 (m, 5H, Ph), 7.9 (s, 3H, NH$_3^+$)

Compound 5e$_4$ (3R,4R)-3-Amino-4-mercapto-6-phenylhexane-1-sulfonic acid

Yield: 53%. [α]$^{20}_D$=+30.5 (c=0.1, H$_2$O). HPLC (gradient 10-90% B in 30 min): Rt=12.67 min. ES-MS[M+Na]$^+$ 312 14. $^1$H NMR (DMSO-D$_6$+TFA): 1.65 (m, 1H, CH$_2$CHS), 1.87 (m, 1H, CH$_2$CHS), 1.97 (m, 2H, CH$_2$C—NH$_2$), 2.6 (m, 3H, CH$_2$SO$_3$H, CH$_2$Phe), 2.8 (m, 1H, CH$_2$Phe), 2.93 (m, 1H, CHSH), 3.4 (m, 1H, CHNH$_2$), 7-7.3 (m, 5H, Ph), 7.9 (s, 3H, NH$_3^+$).

EXAMPLE 1

Synthesis of the Dimeric Compound 5e

A 0.1M aqueous solution of iodine is added, dropwise, until the coloration persisted, with stirring at 25° C., to compound 5e (1 equivalent) in solution in ethanol (0.1 ml/mmol). After concentration under reduced pressure, the oil crystallizes in the presence of ether. The product is dried under reduced pressure after filtration.

The dimeric compound 5e was characterized by means of its $^1$H NMR spectrum in DMSO-D$_6$ at 400 MHz and by electrospray mass spectrometry.

Dimeric Compound 5e 4,4'-Dithiobis-(3,3'-amino-6,6'-phenyl-1,1'-hexane-sulfonic)acid Yield 85%. $^1$H NMR (DMSO-D$_6$): 1.6 (m, 2H, CH$_2$—CH—S), 1.7-2.0 (m, 6H, CH$_2$—CH$_2$—CH—S, CH$_2$CH$_2$—SO$_3$), 2.6-2.8 (m, 8H, CH$_2$—CH—S, CH$_2$CH$_2$—SO$_3$, CH$_2$—CH—S), 2.9-3.2 (m, 2H, CHS), 3.6 (m, 2H, CH—N), 7.1 (m, 10H, H aromatic), 7.9-8.1 (m, 6H, NH$_3^+$). ES$^-$: 275 M–H$^+$. ES$^+$: 599 M+Na$^+$.

EXAMPLE 2

Determination of the Inhibition Constants of the Compounds with Respect to APA

The compounds 5 were tested, in vitro, on recombinant aminopeptidase A in order to determine their affinity for APA.

The assaying of APA activity is based on the protocol of Goldberg, adapted to the microplate assay scale (Pro Bind® 3915) (Chauvel et al., J. Med. Chem., 1994, 37, 1339-1346).

Principle

In vitro, in the presence of calcium ions, APA hydrolyzes α-L-glutamyl-β-naphthylamide (gluβNa) to glutamate and β-naphthylamine (βNa). A diazotization reaction in an acidic medium makes it possible to visualize the β-naphthylamine by formation of a violet-colored complex: spectrophotometric measurement then makes it possible to determine the amount of complex formed and, by reference to a standard curve produced with increasing concentrations of β-naphthylamine, to deduce therefrom the enzymatic activity of the sample.

Reagents

The GluβNa substrate and the β-naphthylamine (Bachem) are solubilized in dimethyl sulfoxide and 0.1N HCl, respectively, and conserved at −20° C. at a concentration of 10$^{-2}$M. The diazotization reaction is carried out in the presence of sodium nitrite (87 mM), of ammonium sulfamate (130 mM) and of N-(1-naphthyl)ethylenediamine dihydrochloride (23 mM).

Enzymatic Reaction

The reaction takes place at pH 7.4 in 50 mM Tris-HCl buffer, in the presence of calcium (4 mM CaCl$_2$); the sample to be assayed is incubated at 37° C. in the presence of a substrate (200 μM GluβNa) and in the presence or absence of various concentrations of the inhibitor to be tested, in a final volume of 100 μl. The reaction is stopped by the addition of 10 μl of 3N HCl. A standard curve for β-naphthylamine in an acidic medium (addition of 10 μl of 0.1N HCl) is produced in parallel.

Visualization of the Product Formed

The following are added to each well:

25 μl of sodium nitrite (mix, wait 5 min at ambient temperature),

50 μl of ammonium sulfamate (stir, wait 5 min at ambient temperature), then

25 μl of 23 mM N-(1-naphthyl)ethylenediamine dihydrochloride (mix, wait for the violet color to stabilize for approximately 30 min at 37° C.).

The absorbance is subsequently measured at 540 nm.

The compound EC 33 ((S)-3-amino-4-mercaptobutylsulfonic acid) described in application WO 99/36066), a monomer of the compound RB 150 (4,4'-dithiobis-3-aminobutane-1-sulfonic acid) described in application WO 2004/007441, was used as a reference compound.

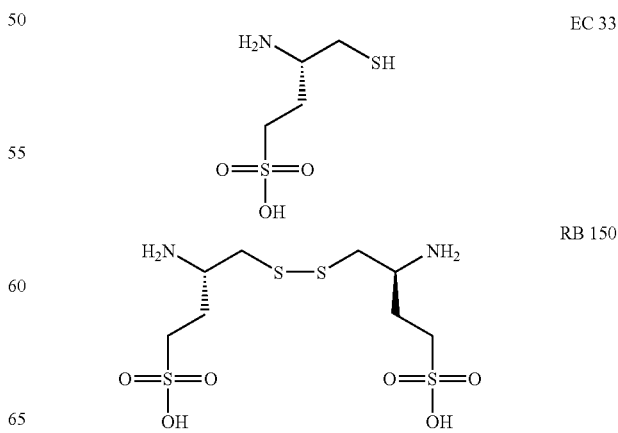

The results are given in tables 1 and 2 hereinafter.

TABLE 1

| | Compounds | | | | |
|---|---|---|---|---|---|
| | EC 33 | 5a | 5b | 5c | 5d |
| Ki (µM) | 0.304 | >100 | 8.00 | 4.00 | 0.380 |
| | Compounds | | | | |
| | EC 33 | 5e | 5f | 5g | 5h |
| Ki (µM) | 0.304 | 0.08 | 0.092 | 0.096 | 0.110 |

The results show that compounds 5d, 5e, 5f, 5g and 5h, which have a $C_1$ or $C_2$ alkyl chain $R_2$ substituted with an optionally substituted phenyl group, exhibit an inhibitory activity of the same order as or greater than that of the reference compound.

TABLE 2

| | Compounds | | | | |
|---|---|---|---|---|---|
| | EC 33 | 5e1 | 5e2 | 5e3 | 5e4 |
| Ki (µM) | 0.304 | 1.92 | 0.03 | 1.04 | 0.84 |

The results show that compound 5e2, of (S), (S) configuration, exhibits the highest APA-inhibiting activity, greater than that of the reference compound by a factor of 10.

The invention claimed is:

1. Compound characterized in that it corresponds to formula (1)

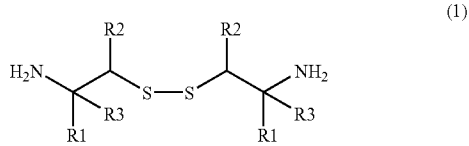

(1)

in which
each group $R^1$ is identical to the other group $R^1$ and represents:
  a $C_1$ to $C_6$ alkyl, $C_2$ to $C_6$ alkenyl or $C_2$ to $C_6$ alkynyl group,
  a $(CH_2)_n$benzyl group in which n is equal to 0 or 1,
  a $(CH_2)_m(C_3$ to $C_6$ cycloalkyl) group in which m is equal to 0 or 1,
each of the alkyl, alkenyl, alkynyl, benzyl or cycloalkyl groups being substituted with one or two group(s) represented by the group A;
the group A represents:
  a carboxylate group COOH or COOR, R representing a $C_1$ to $C_6$ alkyl or $CH_2$phenyl group;
  a sulfonate group $SO_3H$ or $SO_3R'$, R' representing a $C_1$ to $C_6$ alkyl or $CH_2$phenyl group;
  a phosphonate group $PO_3H_2$ or $PO_3R_2"R'''$, R" and R''' independently representing H, or a $C_1$ to $C_6$ alkyl or $CH_2$phenyl group;
each group $R^2$ is identical to the other group $R^2$ and represents a $C_1$ to $C_6$ alkyl, $C_2$ to $C_6$ alkenyl or $C_2$ to $C_6$ alkynyl group, each alkyl, alkenyl or alkynyl group being free or substituted with the group B;
the group B represents:
  a carboxylate group, COOH or COOR', R' representing a $C_1$ to $C_6$ alkyl or $CH_2$phenyl group;
  a phenyl group that is free or substituted with one or more radicals chosen from a halogen atom, an optionally protected hydroxyl radical, a $C_1$ to $C_4$ alkyl group, a cyano group, a free, salified or esterified carboxyl group or an amide group;
each group $R^3$ is identical to the other group $R^3$ and represents a hydrogen atom.

2. Compound according to claim 1, characterized in that $R^1$ is chosen from $C_1$ to $C_6$ alkyl, $C_2$ to $C_6$ alkenyl and benzyl groups, each of these groups being substituted with one or two group(s) represented by the group A as defined in claim 1.

3. Compound according to either of claims 1 and 2, characterized in that $R^2$ is chosen from a $C_1$ to $C_6$ alkyl group and a $C_2$ to $C_6$ alkenyl group, it being possible for each of these groups to be substituted with one or two group(s) represented by the group B as defined in claim 1.

4. Compound according to claim 1, characterized in that $R^1$ represents an ethyl group substituted with a sulfonic group, a phosphonic group or a carboxylic group, that is free, salified or esterified, and $R^2$ represents an ethyl group substituted with a free or substituted phenyl group.

5. Compound according to claim 1, characterized in that it is 4,4'-dithiobis-(3,3'-amino-6,6'-phenyl-1,1'-hexanesulfonic) acid.

6. Compound according to claim 5, characterized in that it is 4(S),4'(S),3(S),3'(S)-4'-dithiobis-(3,3'-amino-6,6'-phenyl-1,1'-hexanesulfonic) acid.

7. Pharmaceutical composition, characterized in that it comprises a compound according to claim 1.

8. A method of selectively inhibiting aminopeptidase A, which comprises administering to a patient in need thereof an efficient amount of a compound of formula (1) according to claim 1.

9. A method for treating arterial hypertension which comprises administering to a patient in need thereof an efficient amount of a compound of formula (1) according to claim 1.

10. A method for treating a disease selected from the group consisting of primary or secondary arterial hypertension, cardiac insufficiency and renal insufficiency, myocardial infarction diabetic proteinuria, which comprises administering to a patient in need thereof an efficient amount of a compound of formula (1) according to claim 1.

11. A method according to claim 8, wherein the compound of formula (1) is 4,4'-dithiobis-(3,3'-amino-6,6'-phenyl-1,1'-hexanesulfonic) acid.

12. A method according to claim 8, wherein the compound of formula (I) is 4(S),4'(S),3(S),3'(S)-4'-dithiobis-(3,3'-amino-6,6'-phenyl-1,1'-hexanesulfonic) acid.

13. A method according to claim 10, wherein the compound of formula (1) is 4,4'-dithiobis-(3,3'-amino-6,6'-phenyl-1,1'-hexanesulfonic) acid.

14. A method according to claim 9, wherein the compound of formula (1) is 4(S),4'(S),3(S),3'(S)-4'-dithiobis-(3,3'-amino-6,6'-phenyl-1,1'-hexanesulfonic) acid.

15. A method according to claim 10, wherein the compound of formula (1) is 4,4'-dithiobis-(3,3'-amino-6,6'-phenyl-1,1'-hexanesulfonic) acid.

16. A method according to claim 10, wherein the compound of formula (1) is 4(S),4'(S),3(S),3'(S)-4'-dithiobis-(3,3'-amino-6,6'-phenyl-1,1'-hexanesulfonic) acid.

* * * * *